United States Patent
Liong et al.

(10) Patent No.: US 11,434,468 B2
(45) Date of Patent: Sep. 6, 2022

(54) LACTIC ACID BACTERIA AND ITS APPLICATIONS

(71) Applicant: Bened Biomedical Co., Ltd., Taipei (CN)

(72) Inventors: Mintze Liong, Penang (MY); Ying-Chieh Tsai, Taiwan (CN); Matthew Cheeyuen Gan, Penang (MY); Sawibah Yahya, Penang (MY); Sybing Choi, Penang (MY); Jiasin Ong, Penang (MY); Waiyee Low, Selangor (MY); Chih-Chieh Hsu, Taipei (CN); Yi-Shan Lee, Taipei (CN)

(73) Assignee: Bened Biomedical Co., Ltd., Taipei (TW)

( * ) Notice: Subject to any disclaimer, the term of this patent is extended or adjusted under 35 U.S.C. 154(b) by 0 days.

(21) Appl. No.: 16/477,723

(22) PCT Filed: Jan. 13, 2017

(86) PCT No.: PCT/CN2017/071181
§ 371 (c)(1),
(2) Date: Jul. 12, 2019

(87) PCT Pub. No.: WO2018/129722
PCT Pub. Date: Jul. 19, 2018

(65) Prior Publication Data
US 2020/0087741 A1   Mar. 19, 2020

(51) Int. Cl.
| | | |
|---|---|---|
| *C12N 1/20* | (2006.01) | |
| *A61K 35/747* | (2015.01) | |
| *A61K 38/00* | (2006.01) | |
| *C07K 14/335* | (2006.01) | |
| *C12R 1/225* | (2006.01) | |

(52) U.S. Cl.
CPC ............ *C12N 1/205* (2021.05); *A61K 35/747* (2013.01); *C07K 14/335* (2013.01); *C12N 1/20* (2013.01); *A61K 38/00* (2013.01); *C12R 2001/225* (2021.05)

(58) Field of Classification Search
None
See application file for complete search history.

(56) References Cited

U.S. PATENT DOCUMENTS

| | | | | |
|---|---|---|---|---|
| 2004/0022779 A1* | 2/2004 | Rudel | ............... | C07K 14/4747 424/94.63 |
| 2015/0306157 A1 | 10/2015 | Tsai | | |
| 2015/0343003 A1* | 12/2015 | Kullisaar | ............... | A61P 29/00 424/456 |

FOREIGN PATENT DOCUMENTS

TW   201540835 A   11/2015

OTHER PUBLICATIONS

Yan, F. et al. 2007. Soluble proteins produced by probiotic bacteria regulate intestinal epithelial cell survival and growth. Gastroenterology 132: 562-575. specif. p. 562.*
Liu, J. et al. 2015. Neuroprotective effects of Clostridium butyricum against vascular dementia in mice via metabolic butyrate. BioMed Research International, Article ID: 412946, pp. 1-12. specif. pp. 1, 2.*
Ellis, J.M. et al. 2017. Current approaches to the treatment of Parkinson's disease. Bioorganic & Medicinal Chemistry Letters 27: 4247-4255; specif. pp. 4247, 4248, 4249, 4353.*
Meerman, S. 2017. ADHD: a critical update for educational professionals. International Journal of Qualitative Studies on Health and Well-Being 12: 1-7; specif. pp. 1, 2, 3, 4.*
McColgan, P. et al. 2018. Huntington's disease: a clinical review. European Journal of Neurology 25: 24-34; specif. pp. 24, 28.*
Taiwanese Office Action dated May 12, 2020 with English Translation of Search report.
A J Cox et al., "Oral administration of the probiotic Lactobacillus fermentum VRI-003 and mucosal immunity inendurance athletes", Br J Sports Med vol. 44, pp. 222-226, 2010.
Alexander Lin et al., "Hypnotic Effects of Lactobacillus fermentum PS150 on Pentobarbital-Induced Sleep in Mice", Nutrients 2019, vol. 11-2409, pp. 1-13.

* cited by examiner

*Primary Examiner* — Olivia M. Wise
*Assistant Examiner* — Sharon M. Papciak
(74) *Attorney, Agent, or Firm* — Fishman & Associates, LLC

(57) ABSTRACT

The invention relates to a lactic acid bacterium (LAB), *Lactobacillus fermentum* PS150, and a bioactive protein produced by the LAB, which has an advantageous effect in improving mood disorder, enhancing cognitive functions in brain and treating or preventing a neurodegenerative disease.

5 Claims, 11 Drawing Sheets

Specification includes a Sequence Listing.

(a)

(b)

(a)

(b)

(a)

(b)

(c)

(a)

(b)

(a)

(b)

LACTIC ACID BACTERIA AND ITS APPLICATIONS

FIELD OF THE INVENTION

The invention relates to a probiotic and a composition comprising the same. Particularly, the invention relates to a new lactic acid bacteria and its specific use in improving a mood disorder or a neurological condition and treating or preventing a disease related to apoptosis of neurons or neurodegeneration.

BACKGROUND OF THE INVENTION

Fermented food products contain various useful bacteria, including lactic acid bacteria (LAB). Various strains of LAB are used in the manufacture of fermented foods, including milk, bread, vegetables, and other edible plant materials. LAB is a group of Gram-positive bacteria generally used in the production of fermented foods. The benefits of LAB in dietary and clinical applications have been widely studied. LAB have been utilized as fermenting agents for the preservation of food taking benefit of a low pH and the action of fermentation products generated during the fermentative activity thereof to inhibit the growth of spoilage bacteria. To this end, LAB have been used for preparing a variety of different foodstuff such as cheese, yogurt and other fermented dairy products from milk. It has attracted a great deal of attention in that LAB have been found to exhibit valuable properties to man and animals upon ingestion. In particular, specific strains of the genus *Lactobacillus* or *Bifidobacterium* have been found to be able to colonize the intestinal mucosa and to assist in the maintenance of the well-being of man and animal. Anti-inflammatory activity and the immunomodulatory activity are well-known characteristic of LAB. U.S. Pat. No. 7,875,421 pertains to the use of the DNA sequence of a *Lactobacillus johnsonii* strain, in particular to its genomic sequence for elucidating interactions of microorganism with hosts they colonize, and moreover for elucidating the basis of probiotic properties exhibited by such strain.

Psychiatric disorders which are on the increase globally already rank among the leading causes of disability. Mood disorders are common, chronic mental illnesses. A person can be considered to be suffering a mood disorder, which is also known as an affective disorder, if their moods are characterised by sustained extremes in both intensity and/or type. Sleep disturbances are among the most common symptoms in patients who have acute episodes of mood disorders, and patients who have mood disorders exhibit higher rates of sleep disturbances than the general population, even during periods of remission (Psychiatr Clin North Am. 2006 December; 29(4): 1009-32).

One of the main physiological systems involved in the regulation of the stress response are the hypothalamus-pituitary adrenal. Various stressful stimuli are known to activate the hypothalamic-pituitary-adrenal axis to release glucocorticoids in the circulation. Glucocorticoid is a crucial integral hormonal mediator of the body's response to stress and speculated to play a role in the ability of stress to promote disease. Lactic acid bacteria have been well documented for their role in maintaining a healthy gut. However, the roles of gastrointestinal microbiota in alleviating disorders occurs outside the gut have gained much attention.

SUMMARY OF THE INVENTION

The invention relates to a new lactic acid bacteria (LAB), *Lactobacillus fermentum* PS150, and a bioactive protein produced by the LAB and their advantageous effect in improving a mood disorder or a neurological condition and treating or preventing a neurodegenerative disease.

The invention provides an isolated LAB, which is *Lactobacillus fermentum* PS150 (PS150) having any of the nucleic acid sequences as shown in SEQ ID NOs:1 to 3. The invention also provides an isolated LAB, which has been deposited with Deutsche Sammlung von Mikroorganismen and Zellkulturen, DSMZ, located at Inhoffenstr. 7B, D-38124 Braunschweig, under Budapest Treaty on 6 Jun. 2016 and was given the accession number DSM 32323.

The invention also provides a protein fraction, which are obtained from extracellular protein of the PS150 cells, and comprises a EF-Tu protein having the amino acid sequence of SEQ ID NO:4. Surprisingly, the invention firstly identifies that the EF-Tu protein is effective in improving a mood disorder, a neurological condition and a neurodegenerative disease.

The invention also provides a composition comprising the PS150 cells, the EF-Tu protein of the invention or the protein fraction of the PS150 of the invention and optionally an edible carrier or a pharmaceutically acceptable carrier. The compositions of the invention can be in any form suitable for administration, in particular oral administration. This includes for instance solids, semi-solids, liquids, and powders.

The invention also provides a use of a PS150 cell of the invention or a composition containing the same in the manufacture of a preparation for improving a mood disorder or a neurological condition, or treating or preventing a disease related to apoptosis of neurons or neurodegeneration. In one embodiment, the PS150 cells are in an amount ranging from about $10^5$ to about $10^{13}$ colony forming units (cfu). The invention further provides a use of a protein fraction of the invention or a composition containing the same in the manufacture of a preparation for improving a mood disorder or a neurological condition, or treating or preventing a disease related to apoptosis of neurons or neurodegeneration. In one embodiment, the protein fraction is in an amount ranging from about 15 mg/kg to about 500 mg/kg. The invention further provides a use of a EF-Tu protein or a composition containing the same in the manufacture of a preparation for improving a mood disorder or a neurological condition, or treating or preventing a disease related to apoptosis of neurons or neurodegeneration.

The embodiments of mood disorder or a neurological condition include, but are not limited to, anxiety, depression, stress and brain cognition.

DETAILED DESCRIPTION OF THE INVENTION

Figure 1:
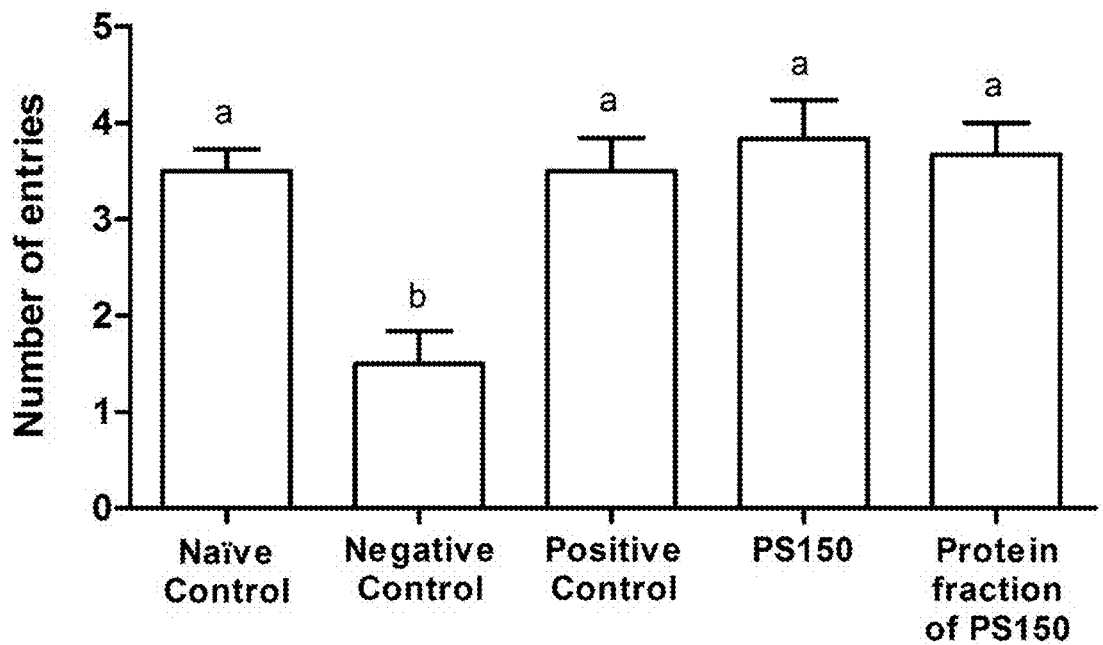
FIGS. 1 (a) and (b) show that anxiety behavior of rats is assessed using elevated plus maze after 4 weeks of chronic mild stress protocol; (a) Number of entries into the open arms observed in rats on elevated plus maze; (b) Ratio of time spent on the closed arms to the time spent on the open arms. Nave control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; *L. fermentum* PS150 group, where rats were subjected to chronic mild stress and given 200 μL PBS containing 1×10⁹ cfu viable *L. fermentum* PS150; Protein fraction of *L. fermentum* PS150 group, where rats were subjected to chronic mild stress and given 200 μL PBS containing 300 mg/kg protein. Error bars represent standard of means; n=6. $^{ab}$ A significant difference in the number of entries of rats into the open arm of EPM (a) and ratio of time spent on the closed arms to the time spent on the open arms (b) between different groups; P<0.05.
Figure 1:
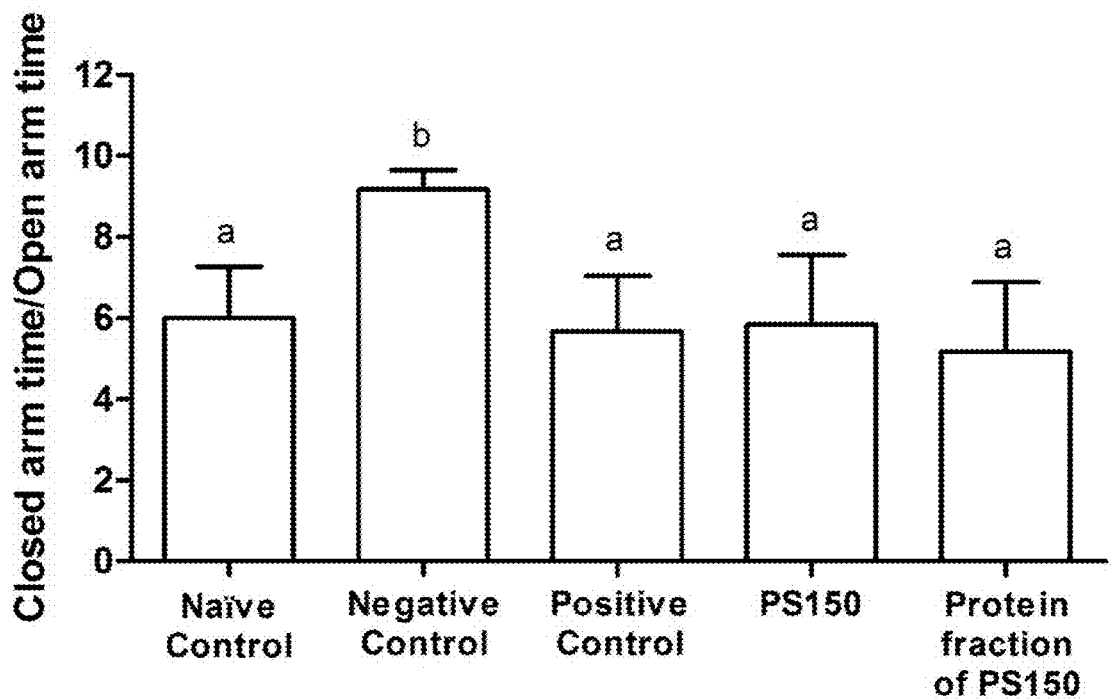

The present invention surprisingly founds a new lactic acid bacteria (LAB), Lactobacillus fermentum PS150, and a bioactive protein produced by the LAB has advantageous effect in improving mood disorder or neurological conditions and treating or preventing a neurodegenerative disease.

Definitions

Terms not specifically defined herein should be understood according to the meaning that would be given to them by one of skill in the art in light of the disclosure and the context. As used in the specification, however, unless specified to the contrary, the following terms have the meaning indicated according to the following conventions.

The abbreviations listed herein are as follows:
CDS: Coding sequence; COG: Clusters of Orthologous Group; CRISPR: Clustered regularly-interspaced short palindromic repeats; EF-Tu: Elongation factor Tu; GO: Gene ontology; HGAP: Hierarchical Genome Assembly Process.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

As used herein, the terms "a," "an," and "the" are to be understood as meaning both singular and plural, unless explicitly stated otherwise. Thus, "a," "an," and "the" (and grammatical variations thereof where appropriate) refer to one or more.

The term "probiotic" is recognized in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species.

The term "pharmaceutically acceptable" as used herein refers to compounds, materials, compositions, and/or dosage forms which are, within the scope of sound medical judgment, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The term "edible carrier" refers to compounds, materials, compositions, and/or dosage forms which are, suitable for use in contact with the tissues of a subject. Each carrier must also be "acceptable" in the sense of being compatible with the other ingredients of the formulation.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment.

As used herein, the term "disorder" is used interchangeably with "disease" or "condition."

As used herein, the term "mood disorder" is described in DSM-IV-TR and is a category of illnesses that describe a serious change in mood. Illness under mood disorder include: major depressive disorder, bipolar disorder (mania—euphoric, hyperactive, over inflated ego, unrealistic optimism), persistent depressive disorder (long lasting low grade depression), cyclothymia (a mild form of bipolar disorder), and SAD (seasonal affective disorder).

As used herein, the term "neurological condition" is a category of illnesses that describe the impact of neurological damage and disease on brain function in terms of behavior, memory or cognition. Illness under neurological condition includes but is not limited to stress (such as chronic mild stress), cognitive decline, cognitive impairment (including mild cognitive impairment (MCI)), memory lapses, general recall issues, cognitive disorders, or a neurodegenerative disease such as Alzheimer's disease, Huntington's disease, Parkinson's disease, dementia, amyotrophic lateral sclerosis, stroke, and schizophrenia.

The term "treatment" is understood as meaning to lessen or decrease at least one sign, symptom, indication, or effect of a specific disease or condition. As used herein, "prevention" is understood as to limit, reduce the rate or degree of onset, or inhibit the development of at least one sign or symptom of a disease or condition.

As used herein, the term "subject" is any animal that can benefit from the administration of a compound or composition as disclosed herein. In some embodiments, the subject is a mammal, for example, a human, a primate, a dog, a cat, a horse, a cow, a pig, a rodent, such as for example a rat or mouse. Typically, the mammal is a human.

Lactic Acid Bacteria

In one aspect, the invention provides an isolated LAB, which is *Lactobacillus fermentum* PS150 (PS150) having any of the nucleic acid sequences as shown in SEQ ID NOs:1 to 3. The sequences of SEQ ID NOs:1 to 3 are listed below.

biogenesis) and 136 CDS in category K (transcription). Moreover there were nine prophage regions identified and interestingly, four of them are predicted as intact prophages. Searches for antibiotic resistance genes revealed six candidate resistance genes that include 30S ribosomal protein S12, maltose O-acetyltransferase, galactoside O-acetyltransferase, putative acetyltransferase, chloramphenicol acetyltransferase and thymidylate synthase. Chromosomes comparisons among bacterial strains can reveal genomic features that are unique to certain strains. It shows that the LAB of the invention has unique 98 protein-coding sequences. Out of the 98 sequences, 35 of them encode for hypothetical

| No. | Gene Description | Gene Sequence |
|---|---|---|
| 1 | Putative glycosyltransferase EpsJ | Atgaggaacaatcaaagtaacacgccgctaatttcagtgattattcctgcatataaagtcgaaaaatacttag cgttttgtgttgaatcagttgttgcacaaactttaactggttatgaagtgattattgtcgatgatggctcacc agataatactggagagatcacggatcacttagcgcaacaatatgaagcggttaaggtgattcatcaagaaaac gcaggagttagtaccgcacggaatacggggattgacaacgctcaagggaaatatattacttttattgatggtg atgattttatcgctccgacttttctggagtatatggttaatatggtagagaaaaccattcggatttcggact ggctctagattgttttacgaagaatgatgagaaacctttggatcaaactgaagataaagtgtatgctccagaa aaggcggtaagtttgttgctatccccacgtgtaattgttggctgttag (SEQ ID NO: 1) |
| 2. | Putative glycosyltransferase EpsF | Gtgaatgatgttccatcaccgtactatgatgaaattatagaacggggttcaaaaatattcattctgccgcaat aaataacgtttaccatcattatcaggaatgcaaaaagatattacgagatggggattacgatgttgtttgtgat aacaacttgattaaatccatcccaatgatgcttgctgctaagaaatgtggagttcctgtacggattttgcata gtcacaacacgaaattaagcacaatcatcaagaaggaatggattacgaagctcctattgccattattgaaaag ggaaattacagattattgtgcatgcggccaactagctggggaagcactatttgggaaagctaagtttacggtt attccaaatgtaatctcaccagaaacgaacacctttgataaagtcaagagagataaaatcagaaaagagcttg gcgttgacgataaggttgttgtagggactgttggtcggacatctatacaaaaaaaccccttatttcgcaattga tgtaattgagaaggtacaccaaagtaatcctagtattgtttattggtggattggtagtggtgaactagatgat caactgagagcgtacgtagaaaagaagggggttaggtaaggttgtatctttcctaggaagtagggatgatgttc aagatctttaccaggcaatggatgtattcttttttaccctcgcttttttgaaggtttaccactaactggagttga agctcaagcaatggggttaccgtcgattttatcagctagcgttacagatagattggtatataccgatctggta aagtacgtatcttggatgaacctatcgaagaatgggaaaaagcttttaaaaaagcgatcgaacggattccaca aaggagggcaatatacaaagaacttaagcagagcgtttattcagctgaagatgcgggaaagaatatgacaaag atttacgaggatcttctcgcctcaaaaattgcggtaa (SEQ ID NO: 2) |
| 3 | Putative glycosyltransferase EpsF | Ttgattcggatattacaattaccaaacactatttctgagaaaatggtcgcatgtcagtaattatgagtatata taggcacatagatagaaccaagattcagtttgattttgcggtatctgagtctagtggcgatacttatcttgat gaaattaaaaagctttggaggcaaggtatttgtgattccatctggcgaggtttcctacaaaagtgttgtcaag atggttaatatgctccttaagaaaagagagtattcatttatacattatcacgcaatctcaattggggagttgc tctaaacgttgcacatccggcatggtgtaaagataatcacacacatcatgcaacatattttagcgatggattta tgaagtcaattcgaaatcgaatcttttctctaaatataaagttatattcagataagttggcagctgtttcccc agaagcgggtagaactttatttggaaaaacaacaatatatatatataccaaatgtaattaattataaaaaaat atactttctcgcgtaataatagagaaaaaattcgtcggcaatataacattgatgatggtgactttgtcgttgg tcatgtaggacgtctgtcaaaacaaaaaaaccatcaatttctgatcagagccttagtctattacatgcatcg gcggaaaagtacaaattaatgctcgtgggtagtggaccactcgaaaatgatctgaggacacttgtaagtcaac tgaatattgaaaggtcagttattttttgttggtgcaaagcaagatgtaactgcgttttattcagcatttgactt gttctggttaccttccttgtatgagggattgcctacggttggattggaagcgcattctaacggtctttcaatc attgcaagtgatcgtatttcacctgagctagccattgaaaatgttattttttctccaattaggcataaaagcg atttacaaaaatggtgtcatatcactctggagcgagattggcctcgctctacagatgtcatgcggacgattga acatagtcggtataattatcaacatgtcttagatcaatggaaaagcctatatgatatgaagtaa (SEQ ID NO: 3) |

The *L. fermentum* PS150 has a circular chromosome of 2,238,401 bp and its GC content is 51%. A total of 2,281 genes were predicted, which was made up of 2,206 protein coding genes, 59 tRNAs, 15 rRNAs and one tmRNA. In addition, two clustered regularly-interspaced short palindromic repeats (CRISPR) regions are found, which may provide immunity against foreign genetic elements. Of the 2,206 protein coding genes, 465 were predicted as hypothetical proteins with no functions ascribed to them. Based on Clusters of Orthologous Group (COG) functional categorization, 2005 protein coding genes (i.e. 91% of all predicted coding sequence (CDS)) could be assigned to COG functional categories. Of the 2005 protein coding genes, 62% of them belonged to five major COG categories: 447 CDS in category S (function unknown), 364 CDS in category L (replication, recombination and repair), 162 CDS in category E (amino acid transport and metabolism), 140 CDS in category J (translation, ribosomal structure and proteins, which means they have unknown functions or perhaps wrongly predicted as genes. The remaining 63 genes have predicted protein products that include three putative glycosyltransferases that are found in a cluster of genes in a span of less than 15 kb. The representative sequences among the 98 sequences are listed in SEQ ID NOs:1-3.

In one embodiment, the invention provides an isolated and purified lactic acid bacteria, which is *Lactobacillus fermentum* PS150 (PS150), which has been deposited with Deutsche Sammlung von Mikroorganismen and Zellkulturen under Budapest Treaty on 6 Jun. 2016 and was given the accession number DSMZ 32323.

*Lactobacillus fermentum* PS150 is a probiotic strain isolated from fermented meat sausage.

The PS150 is effective in improving a mood disorder or a neurological condition, and treating or preventing a neurodegenerative disease.

Protein Fraction of the PS150 and EF-Tu Protein Purified Therefrom

In another aspect, the invention provides a EF-Tu protein of the PS150, comprising an amino acid sequence of SEQ ID NO:4.

SEQ ID NO: 4
MAEKEHYERTKPHVNIGTIGHVDHGKTTLTAAITKVLAAKGLAKAEDY

SDIDAAPEEKERGITINTAHVEYETEKRHYAHIDAPGHADYVKNMITG

AAQMDGAILVVAATDGPMPQTREHILLARQVGVEYIVVFLNKTDLVDD

DELVDLVEMEVRDLLSEYDFPGDDVPVVRGSALKALEGDPEQEQVVLH

LLDVVDEYIPTPKRPTDKPFMMPVEDVFTITGRGTVASGRIDRGTVKI

GDEVEIVGLKEDVIKSTVTGVEMFHKTLDLGEAGDNVGVLLRGVSHDQ

IERGQVLAEPGSIQTHKQFKGEVYVMTKEEGGRHTPFFSNYRPQFYFH

TTDVTGTIELPDGVEMVMPGDNVTFTVELQKPVALEKGLKFTIREGGH

TVGAGVVSEVLD

In another aspect, the invention provides a protein fraction, which are obtained from extracellular protein of the PS150 cells, and comprises a EF-Tu protein having the amino acid sequence of SEQ ID NO:4 or a functional fragment thereof.

The protein fraction is extracellular protein from *L. fermentum* PS150. The protein fraction of *L. fermentum* PS150 is isolated and purified by, for example, gelfree fractionation and reversed-phase high performance liquid chromatography, and identified by MALDI-TOF mass spectrometry analysis. The invention surprisingly found a purified protein fraction with a molecular weight of approximately 55 kDa, which is subsequently identified as an elongation factor Tu with 396 amino acids residues (SEQ ID NO:4), exhibits an efficacy in improving a mood disorder or a neurological condition and a neurodegenerative disease.

A gene named tuf, which encodes for EF-Tu, was found as a probiotic factor in *L. fermentum* PS150. The discovery of this important gene that confers positive brain health effects was achieved by determining the identity of peptide sequences from a bioactive fraction, in which there was only one clear hit with 100% identity and BLASTP e-value of $1e^{-5}$ to the predicted proteome of *L. fermentum* PS150. The hit was EF-Tu and hence, a detailed investigation on its molecular evolution was conducted to identify putative residues that might be involved in protein-protein interaction to elicit the observed health effects.

EF-Tu protein is one of the prokaryotic elongation factors and the elongation factors are part of the mechanism that synthesizes new proteins by translation at the ribosome. Surprisingly, the invention firstly identifies that the EF-Tu protein is effective in improving a mood disorder or a neurological condition and a neurodegenerative disease. Accordingly, the invention provides a method for treating or preventing a neurodegenerative disease, comprising administering an effective amount of a EF-Tu protein to a subject. In one embodiment, the EF-Tu protein is that from the PS150. In another embodiment, the EF-Tu protein is in an amount ranging from about 15 μg/kg to about 500 μg/kg. Preferably, the EF-Tu protein is in an amount ranging from about 15 μg/kg to about 400 μg/kg, about 15 μg/kg to about 350 μg/kg, about 15 μg/kg to about 300 μg/kg, about 15 μg/kg to about 250 μg/kg, about 15 μg/kg to about 200 μg/kg, about 15 μg/kg to about 150 μg/kg, about 15 μg/kg to about 100 μg/kg, about 15 μg/kg to about 50 μg/kg, about 50 μg/kg to about 500 μg/kg, about 100 μg/kg to about 500 μg/kg, about 150 μg/kg to about 500 μg/kg, about 200 μg/kg to about 500 μg/kg, about 250 μg/kg to about 500 μg/kg, about 300 μg/kg to about 500 μg/kg, about 350 μg/kg to about 500 μg/kg or about 400 μg/kg to about 500 μg/kg.

The residues (40K, 41G, 42L, 44K, 46E, 161E, 185E, 195D, 327S, 345E and 360T) represent putative binding sites that may be the key distinguishing factors of *L. fermentum* PS150 EF-Tu in terms of its brain health effects.

The EF-Tu protein of the invention can reduce TNF-alpha which contribute to the pathogenesis of neurodegenerative via stimulation of the indoleamine 2,3-dioxygenase (IDO). This eventually reduces the turnover rate of tryptophan to kynurenine, and lead to increased production of serotonin. The EF-Tu protein also reduces the plasma corticosterone level and thus contributes to the alleviation of anxiety, depression and stress.

Compositions and Applications

In another aspect, the invention provides a composition comprising the PS150 cells, the EF-Tu protein of the invention or the protein fraction of the PS150 of the invention and optionally an edible carrier or a pharmaceutically acceptable carrier. In the compositions of the invention, said PS150 cells can be used in the form of whole bacteria which may be living or not. Preferably the bacterial cells are present as living, viable cells.

The compositions of the invention can be in any form suitable for administration, in particular oral administration. This includes for instance solids, semi-solids, liquids, and powders.

Examples of the compositions of the invention are nutritional compositions, including food products and in particular dairy products.

The composition can be for example a capsule, tablet, drink, powder or dairy product. Optionally, other strains of LAB may be present. Preferably the present nutritional composition is a baby food, an infant milk formula or an infant follow-on formula. Preferably the present composition is a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, portion or any other form usually not associated with aliments, and which has beneficial effects for one's health. A "functional food" is an aliment which also has beneficial effects for one's health. In particular, food supplements and functional food can have a physiological effect—protective or curative—against a disease.

If the composition according to the invention is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. Preferably, the dietary supplement comprising the composition of the invention is administered in the form of tablets, lozenges, capsules or powders, manufactured in conventional processes of preparing dietary supplements.

The compositions described herein can be pharmaceutically acceptable compositions, which may include one or more pharmaceutically acceptable carriers, excipients, binders, diluents or the like. The instant compositions can be formulated for various routes of administration, for example, by oral administration. They also may be provided in combination with delivery vehicles such as in some encapsulating technology.

For oral administration, powders, suspensions, granules, tablets, pills, capsules, gelcaps, and caplets are acceptable as solid dosage forms. These can be prepared, for example, by mixing one or more compounds disclosed herein with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and compositions may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

In a further aspect, the invention provides a method of improving a mood disorder or a neurological condition or treating or preventing a disease related to apoptosis of neurons or neurodegeneration, comprising administering an effective amount of the PS150 cells of the invention or a composition containing the same to a subject. Accordingly, the invention provides a use of a PS150 cell of the invention or a composition containing the same in the manufacture of a preparation for improving a mood disorder or a neurological condition or treating or preventing a disease related to apoptosis of neurons or neurodegeneration. In one embodiment, the PS150 cells are in an amount ranging from about $10^5$ to about $10^{13}$ colony forming units (cfu). Preferably, the amount of the PS150 cells is from about $10^6$ to about $10^{13}$ cfu, $10^6$ to about $10^{12}$ cfu, about $10^6$ to about $10^{11}$ cfu, about $10^6$ to about $10^{10}$ cfu, about $10^6$ to about $10^9$ cfu, about $10^6$ to about $10^8$ cfu, about $10^6$ to about $10^7$ cfu, about $10^7$ to about $10^{13}$ cfu, about $10^7$ to about $10^{12}$ cfu, about $10^7$ to about $10^{11}$ cfu, about $10^7$ to about $10^{10}$ cfu, about $10^7$ to about $10^9$ cfu, about $10^7$ to about $10^8$ cfu, about $10^8$ to about $10^{13}$ cfu, about $10^8$ to about $10^{12}$ cfu, about $10^8$ to about $10^{11}$ cfu, about $10^8$ to about $10^{10}$ cfu, about $10^8$ to about $10^9$ cfu, about $10^9$ to about $10^{13}$ cfu, about $10^9$ to about $10^{12}$ cfu, about $10^9$ to about $10^{11}$ cfu or about $10^9$ to about $10^{10}$ cfu. More preferably, the amount of the PS150 cells is from about $10^6$ to about $10^{12}$ cfu.

In another further aspect, the invention provides a method of improving a mood disorder or a neurological condition or treating or preventing a disease related to apoptosis of neurons or neurodegeneration, comprising administering an effective amount of a protein fraction of the invention or a composition containing the same to a subject. Accordingly, the invention provides a use of a protein fraction of the invention or a composition containing the same in the manufacture of a preparation for improving a mood disorder or a neurological condition or treating or preventing a disease related to apoptosis of neurons or neurodegeneration. In one embodiment, the protein fraction is in an amount ranging from about 15 mg/kg to about 500 mg/kg. Preferably, the amount of the protein fraction ranges from about 15 mg/kg to about 500 mg/kg, about 15 mg/kg to about 400 mg/kg, about 15 mg/kg to about 300 mg/kg, about 15 mg/kg to about 200 mg/kg, about 15 mg/kg to about 100 mg/kg, about 40 mg/kg to about 500 mg/kg, about 40 mg/kg to about 400 mg/kg, about 40 mg/kg to about 300 mg/kg, about 40 mg/kg to about 200 mg/kg, about 40 mg/kg to about 100 mg/kg, about 80 mg/kg to about 500 mg/kg, about 80 mg/kg to about 400 mg/kg, about 80 mg/kg to about 300 mg/kg, about 80 mg/kg to about 200 mg/kg, about 80 mg/kg to about 150 mg/kg, about 100 mg/kg to about 500 mg/kg, about 100 mg/kg to about 400 mg/kg, about 100 mg/kg to about 300 mg/kg or about 100 mg/kg to about 200 mg/kg. More preferably, the protein fraction is in an amount of range from about 40 mg/kg to about 300 mg/kg.

In another further aspect, the invention provides a method of improving a mood disorder, a neurological condition or treating or preventing a disease related to apoptosis of neurons or neurodegeneration, comprising administering an effective amount of a EF-Tu protein of the invention to a subject. Accordingly, the invention provides a use of a EF-Tu protein or a composition containing the same in the manufacture of a preparation for improving a mood disorder, a neurological condition or treating or preventing a disease related to apoptosis of neurons or neurodegeneration. In one embodiment, the EF-Tu protein is that from the PS150. In another embodiment, the EF-Tu protein is in a dosing amount ranges from about 15 pg/kg to about 500 µg/kg; preferably, about 15 µg/kg to about 400 µg/kg, about 15 µg/kg to about 300 µg/kg, about 15 µg/kg to about 200 µg/kg, about 15 µg/kg to about 100 µg/kg, about 50 µg/kg to about 500 µg/kg, about 50 µg/kg to about 400 µg/kg, about 50 µg/kg to about 300 µg/kg, about 50 µg/kg to about 200 µg/kg, about 50 µg/kg to about 100 µg/kg, about 100 µg/kg to about 500 µg/kg, about 100 µg/kg to about 400 µg/kg, about 100 µg/kg to about 300 µg/kg, about 100 µg/kg to about 200 µg/kg, about 150 µg/kg to about 500 µg/kg, about 150 µg/kg to about 400 µg/kg, about 150 µg/kg to about 300 µg/kg, about 150 µg/kg to about 200 µg/kg, about 200 µg/kg to about 500 µg/kg, about 200 µg/kg to about 400 µg/kg or about 200 µg/kg to about 300 µg/kg.

The mood disorder and neurological condition includes but is not limited to anxiety, depression, sleep disturbance, stress (such as chronic mild stress), cognitive decline, cognitive impairment (including mild cognitive impairment (MCI)), memory lapses, general recall issues, cognitive disorders, or a neurodegenerative disease such as Alzheimer's disease, Huntington's disease, Parkinson's disease, dementia, amyotrophic lateral sclerosis, stroke, and schizophrenia.

The diseases related to apoptosis of neurons or neurodegeneration may be selected from the group consisting of a stroke, Alzheimer's disease, Huntington's disease, Parkinson's disease, Pick's disease, Creutzfeldt-Jakob's disease, Parkinson-ALS-dementia complex, Wilson's disease, multiple sclerosis, progressive supranuclear palsy, neuropathic pain-related bipolar disorders, corticobasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression.

The cells, proteins and protein fractions of the invention can lower expression of the indoleamine 2,3-dioxygenase (IDO), reduces the turnover rate of tryptophan to kynurenine, increase serotonin level and reduce plasma corticosterone level. Accordingly, the cells, proteins and protein fractions of the invention can particularly alleviate anxiety, depression and stress.

The present invention is described in greater detail by the examples presented below, which are preceded by a brief description of the figures. It goes without saying however, that these examples are given by way of illustration of the subject of the invention and do not constitute in any manner a limitation thereto.

EXAMPLES

Materials and Methods 1.0 Bacterial Strains and Growth Conditions

*Lactobacillus fermentum* PS150 was obtained from the culture collection of the Division of Bioprocess Technology, School of Industrial Technology, Universiti Sains Malaysia (Penang, Malaysia), previously isolated from a locally purchased fermented sausage. The bacteria was incubated in de Mann Rogosa Sharpe (MRS) (Biomark, India) broth at 37° C. for 20 hours prior to use. This particular strain is a probiotic and documented for its overall brain health promotion effects.

2.0 DNA Preparation

Genomic DNA of *L. fermentum* PS150 was isolated and purified according to the Microbes Environ., vol. 22, no. 3, pp. 214-222, 2007. The purified DNA obtained was stored at −20° C. prior to genome sequencing.

3.0 Genome Sequencing

Genomic DNA of *L. fermentum* PS150 was sequenced using two different next generation sequencing platforms, which were Pacbio RS II and Illumina HiSeq 2000. On the Pacbio platform, SMRT sequencing was performed on a ~10 kb insert library of genomic DNA from *L. fermentum* PS150 using just a single SMRT Cell with C2-P4 chemistry protocol. The pre-filtered raw DNA sequence data have 489,633,442 bp with an average read length of 3257 bp. The raw sequence data were filtered according to the following criteria; minimum subread length of 500 bp, minimum polymerase read quality of 0.8 and minimum polymerase read length of 100 bp. The post-filtered dataset has approximately 166× coverage for a 2.5 Mbp genome. The filtered data were then subjected to the HGAP method (*Nat. Methods*, vol. 10, no. 6, pp. 563-569, 2013) as implemented on the SMRT portalver 2.3.0.140893 for the purpose of chromosome assembly. Dotplot analysis confirmed that this is a circular genome, which is consistent with the other published strains of *Lactobacillus fermentum* chromosomes.

On the Illumina platform, 500 bp library of genomic DNA from *L. fermentum* PS150 was used for paired end (2×100 bp) sequencing. Library preparation was done as per the manufacturer's protocol (Illumina, "An Introduction to Next-Generation Sequencing Technology," Illumina. Inc., 2011). The sequencer generated a total of 20,522,464 reads, which means on average it has covered each base of a two million base pairs genome more than 1000 times. However, the raw sequencing data needed to be filtered so that only quality sequence data passed through for subsequent analysis. Using FASTQC (available at http://www.bioinformatics.bbsrc.ac.uk/projects/fastqc/) as a sequence quality checking tool, per tile sequence quality was flagged as an issue and thus only the last 2 million reads per each pair end were used as the quality per tile for these reads was good.

These reads were then subjected to TRIMMOMATIC for filtering out low quality bases. The filtered data was assembled using VELVET with the choice of kmer determined using VELVETOPTIMISER (S. Gladman and T. Seemann, "VelvetOptimiser," 2012). The resulting assembly has 262 contigs. These contigs were ordered and aligned to the assembly generated from Pacbio HGAP method using MAUVE (*Genome Res., vol.* 14, no. 7, pp. 1394-403, 2004). Filtered good quality sequence data were also aligned to the HGAP assembled data using the BWA software (*Bioinformatics*, vol. 25, no. 14, pp. 1754-60, 2009). The alignment file was manipulated using SAMTOOLS to produce sorted bam file (*Bioinformatics*, vol. 25, no. 16, pp. 2078-2079, 2009). The mapped reads were visualized using ARTEMIS (*Bioinformatics*, vol. 16, no. 10, pp. 944-945, 2000). Since the assembly made using VELVET on Illumina sequence data contained more contigs than the one made with HGAP method, subsequent analysis on *L. fermentum* chromosome used only Pacbio assembled genome.

4.0 Genome Annotation

The software tool PROKKA was used to annotate protein coding genes, tRNAs, tmRNAs, rRNAs and repeats regions such as CRISPERs (*Bioinformatics, vol.* 30, no. 14, pp. 2068-2069, 2014). Functional classification in terms of gene ontology (GO) for each protein coding genes was done by searching for the best hit in EggNOG cluster of orthologous groups (COGs)(*Nucleic Acids Res.*, vol. 42, no. D1, pp. D231D239, 2014). Protein domains among the predicted proteins were identified using the default e value of 1 against the Pfam database (*Nucleic Acids Res.*, vol. 42, no. D1, pp. D222D230, 2014). Prophage sequences within the genome were predicted using PHAST (*Nucleic Acids Res.*, vol. 39, no. suppl, pp. W347-W352, 2011). In the context of probiotic development, antibiotic resistance is a concern and thus searches for potential resistance genes were done using BLASTP against the comprehensive antibiotic resistance database (*Antimicrob. Agents Chemother.*, vol. 57, no. 7, pp. 3348-3357, 2013). The BLASTP e value threshold was set at less than 1 e$^{-5}$ as the cutoff and hits with more than 60% identity to any genes in the antibiotic resistance database were analyzed. KEGG (Kyoto Encyclopedia of Genes and Genomes) Mapper was used to reconstruct a few metabolic pathways of interests of *L. fermentum* PS150.

5.0 Comparisons of *Lactobacillus fermentum* Genomes

Besides *L. fermentum* PS150, there are four other strains that also have their genomes decoded. Using *L. fermentum* PS150 as a reference strain to the software BRIG [*BMC Genomics*, vol. 12, no. 1, p. 402, 2011], the other four known strains' genomes were aligned to it. The nine prophages regions predicted from PHAST were concatenated as one sequence and it is also aligned to the reference. The upper and lower BLASTN identity thresholds were set at 90% and 70%, respectively.

6.0 Tuf Protein Variability Analysis

For EF-Tu variability analysis, all proteins found from the 235 bacteria species were used as an input for calculation of Shannon Entropy [*Bell Syst. Tech. J.*, vol. 27, no. July 1928, pp. 379-423, 1948]. The Shannon entropy equation provides a way to estimate variability of amino acids sequences along a protein. For a given multiple protein sequence alignment, the Shannon entropy (H) per alignment column number is as below:

$$H(X) = -\sum_{i=1}^{N} p_i \log_2 p_i$$

where H is the entropy value,
X is the alignment column number,
N is the number of amino acid types and a gap character (21)*,
$p_i$ is the frequency of $i^{th}$ character in N,
*note that it is optional whether a gap is included as a character. In this study, a gap is considered as a character.

In addition, at the *Lactobacillus* genus level, there were 25 different species with available genomes. The tuf genes in these 25 species were mined using a similar approach as described above. These proteins were also used as an input for Shannon Entropy calculation. Prior to calculation of entropy, the proteins were first aligned using MAFFT [*Bioinformatics*, vol. 28, no. 23, pp. 3144-3146, 2012] and then manually inspected using CLUSTALX [*Bioinformatics*, vol. 23, no. 21, pp. 2947-2948, 2007]. Then, gaps were removed according to wherever they were found on the *L. fermentum* PS150 EF-Tu. Finally, the trimmed alignment was used to calculate Shannon entropy per position in the alignment by using a custom made R script.

7.0 Cell Culture 7.1 Bacterial and Supernatant Preparation

*Lactobacillus fermentum* P S150 is an isolate from fermented meat sausage. The culture was obtained from Universiti Sains Malaysia microorganism culture collection (Penang, Malaysia). The lyophilized stock culture was prepared in the presence of cryoprotectant (pectin) and stored at dry and cool (−20° C.) place. The lyophilized culture was activated successively 3 times in sterile de Man, Rogosa, and Sharpe (MRS) broth (Hi-Media, Mumbai, India) prior to experimental use. During subculture, the culture was inoculated (10% v/v) into sterilized MRS broth and incubated at 37° C. for 18 h. The cell free supernatant (CFS) was obtained by centrifugation at 3500 g for 15 min (4° C.), neutralised with 10 M NaOH to a pH of 7.0, and then sterilized by filtering through a 0.22 mm filter (Sartorius Stedim, Göttingen, Germany) and immediately used or stored at 20° C. until needed.

7.2 Human Neuroblastoma SH-SY5Y Cell Culture

Neuroblastoma cell line, SH-SY5Y cells were purchased from Korea Cell Line Bank (KCLB; Seoul, Korea). Cells were maintained in high glucose Dulbecco's Modified Eagle Medium (DMEM; Difco, Detroit, Mich., USA) supplemented with 10% heat-inactivated fetal bovine serum (FBS; Gibco Life Technologies Inc, Grand Island, N.Y., USA), 100 U/mL penicillin/streptomycin (Gibco Life Technologies Inc, Grand Island, N.Y., USA). Cultures were seeded into flasks containing supplemented medium and maintained at 37° C. in a humidified atmosphere of 5% $CO_2$ and 95% air.

7.3 Cell Culture Treatment and Cell Viability Assay

The SH-SY5Y cells were seeded into 96-well culture plates at a seeding density $1 \times 10^5$ cells per well. All cells in this study were maintained in 10% serum medium until the dexamethasone (Dex; Sigma-Aldrich, Steinheim, Germany) treatment. Cells were incubated for 24 h to allow attachment to the culture plate before treatment. In order to study the effect of bacterial CFS, 20 µL of bacterial CFS were added into well containing 100 µL of SH-SY5Y cells treated with 25 µM Dex in serum-free medium. The 3-(4, 5 dimethylthiazol-2-yl)-2,5-diphenyl-tetrazolium bromide (MTT; Sigma-Aldrich, Steinheim, Germany) reduction was analyzed 48 h after treatment.

Cell viability was measured by quantitative colorimetric assay with MTT, as described previously by Denizot and Lang (J Immunol Methods. 1986 May 22; 89(2):271-7.). MTT was used for the assessment of neuronal injury. When living cells take up MTT, it is converted from yellow to purple formazan crystals by a cellular dehydrogenase. Briefly, 10% of the MTT-labeling reagent, at a final concentration of 0.5 mg/ml, was added to each well at the end of the treatment period and the plate was placed in a humidified incubator at 37° C. with 5% $CO_2$ and 95% air (v/v) for an additional 6 h period. Then, the insoluble formazan was dissolved with dimethylsulfoxide (DMSO; Sigma-Aldrich, Steinheim, Germany). Colorimetric determination of MTT reduction was measured at 570 nm using microplate reader (Thermo Scientific, Waltham, Mass., US). Control cells treated with unfermented MRS were taken as 100% viability.

8.0 In Vivo Study 8.1 Live Cells and Crude Protein Preparations 8.1.1 *Lactobacillus fermentum* PS150 Live Cells

*Lactobacillus fermentum* PS150 was obtained from the culture collection of Bioprocess Technology, School of Industrial Technology, Universiti Sains Malaysia, Penang, Malaysia. The culture was activated three times in de Mann Rogosa Sharpe (MRS) (Biomark, India) broth at 37° C. for 20 hours prior use. Overnight culture of *L. fermentum* PS150 was subjected to centrifugation at 8000 g for 30 minutes at 4° C. to obtain the cell pellets. Upon obtaining the cell pellet, phosphate buffered saline (1.0M, pH 7.4) was used to wash the cell pellet three times. 10% (v/v) of pectin solution is added to the cell pellet prior freezing overnight at −20° C. The frozen cell pellet was then freeze dried at −55° C. overnight. CFU/g of the freeze-dried cells obtained were determined using pour plate method. Thereafter, the freeze-dried cells were prepared to each individual rats at dosage of 9 log CFU/rat/day. The preparations were stored at −20° C. prior to use.

8.1.2 Crude Protein Extracted from *L. fermentum* PS150 Cell Free Supernatant

Overnight culture of *L. fermentum* PS150 was subjected to centrifugation at 8000 g for 30 minutes at 4° C. to obtain the cell-free supernatant. The supernatant was collected and pH was adjusted to 7.0 with 3.0M sodium hydroxide (NaOH). Crude protein was precipitated by adding 80% w/v of ammonium sulphate into the neutralized cell-free supernatant at 4° C. while stirring and then left overnight at 4° C. The precipitated neutralized cell-free supernatant was subjected to centrifugation at 10000 g for 30 minutes at 4° C. The pellets obtained was re-suspended with sterile distilled water and filtered with 0.22 µM cellulose acetate syringe filter. The crude protein fraction obtained was then subjected to freezing overnight at −20° C. prior to freeze-dry at −55° C. overnight. The freeze-dried crude protein is prepared to each individual rats at dosage of 300 mg/kg. The preparations were stored at −20° C. prior to use.

8.2 Animal

This study was performed at the GLP certified Animal Research Centre, Advanced Medical & Dental Institute (IPPT), Bertam Campus, UniversitiSains Malaysia (USM). 30 male Wistar rats (7-8 weeks old, weighed 180-200 g) were obtained from the Animal Research and Service Center, Main Campus, USM, Penang. Upon arrival, the rats were housed undisturbed (3 animal per cage) under standard laboratory conditions (twelve hour light/twelve hour night cycles (light: 0700-1900, temperature of 19-25° c. and humidity within 30-70% RH) in each standard polypropylene shoebox cages on wood chip bedding. Throughout the experiment, the cage bedding was changed once per two days. The received animals were subjected to one week quarantine in order to monitor daily for the presence of diseases or lice in the animal. Once the animals were ensured to be free from any disease or lice, they were then subjected to one week acclimatization prior to the chronic mild stress protocol and treatments. All rats were given ad libitum access to food and water during quarantine and acclimatization period. The animals' weight were measured and monitored weekly.

8.3 Chronic Mild Stress Protocol

The rats were divided into five groups (with 6 rats per group (n=6)), namely, naïve control, negative control, positive control, live cell treatment group and protein treatment group. All rats were subjected to chronic mild stress protocol (Table 1) except the naïve control group. In the naïve control group, all animals were freed from any treatment. In the negative control group, all animals were fed daily with 0.2 ml phosphate buffered saline (1.0M, pH 7.4). In the positive control group, all animals were fed daily with alprazolam powder at dosage of 0.45 mg/kg suspended in 0.2 ml of phosphate buffered saline (1.0 M, pH 7.4). In the live cell treatment group, all animals were fed daily with 9 log CFU/rat/day of live *L. fermentum* PS150. Lastly in the protein treatment group, all animals were fed daily with freeze-dried protein (300 mg/kg rat/day) prepared as previously described. Oral gavage was performed using 1.5 inches, 20-gauge stainless steel feeding needles with a 2.25 mm ball. The chronic mild stress protocol consists of several stressors and non-stressor period as shown in Table 1 and were scheduled throughout the week, for a total of 28 days.

8.4.1 Morris Water Maze (MWM)

Equipment Setup

The diameter of the MWM used was 210 cm, where the height of the pool was 51 cm with non-reflective interior surfaces. The maze was placed in a room with a video camera set up on top of the maze to capture and record the animal's behavior. The water maze was filled up with water of temperature ranging within 19-22° C. to avoid the rats from getting temperature shock (hypothermia or hyperthermia). Then, a colorless and transparent circular goal or platform (designated as escape platform) with the diameter of 10-12 cm was submerged 1-2 cm below the water surface and ensured with stability to avoid tipping of animal when the rats climb on it.

Escape Latency Assessment

The start locations of the MWM was designated at East, West and South East, while the escape platform is submerge at North East. A consecutive four daily trials were performed using these three start locations. Briefly, the animals were gently placed on the first start locations and allowed to swim freely to search for the escape platform. A maximum of two minutes was given for each animal to perform the search for the escape platform. All rats were dried thoroughly with clean towel after the Morris test before returning them to their respective cage. Time taken by each animal to locate

TABLE 1

Weekly schedule of the chronic mild stress protocol.

| | 0900-1300 | 1300-1400 | 1400-1700 | 1700-0900 |
|---|---|---|---|---|
| Mon | Empty bottle[1] | Oral gavage | Refill water[2] | Cage tilt[3] |
| Tue | No stress[4] | | Replacement of sawdust with sand[5] | Empty cage[6] |
| Wed | Restraint[7] | | Social interaction[8] | Food deprivation[9] |
| Thu | Food restriction[10] | | Foreign cage[11] | No stress |
| Fri | Repeated cold stress (2 × 30 min)[12] | | Red light[13] | Wet cage[14] |
| Sat | No stress | | Sounds of predators[15] | Foreign room[16] |
| Sun | Foreign room | | Strobe light[17] | Water deprivation[18] |

[1]Empty bottle: water bottle was emptied for an hour to restrict the animals from water access
[2]Refill water: water bottle was refilled to allow the animals from water access
[3]Cage tilt: tilting of the cage at 45°
[4]No stress: no stressor was performed during this period
[5]Replacement of sawdust with sand: the wood chip bedding were replaced with sand.
[6]Empty cage: cage of the animals were emptied from wood chip during this period.
[7]Restraint: animals were placed into a soft covered wire net to restrain their movement.
[8]Social interaction: all rats were allowed to interact in a larger cage during this period.
[9]Food deprivation: food were removed from the cages
[10]Food restriction: animals were provided with minimal amounts of food during this period
[11]Foreign cage: the animal were transferred to a new cage
[12]Repeated cold stress: 10 pieces of small ice cubes were placed in the animal's cage and allow to melt for 30 minutes
[13]Red light: the animal in cages were placed in a room equipped with red light
[14]Wet cage: the wood chip bedding was damped with sterile water
[15]Sound of predators: the animal is exposed to sound of predators from recordings
[16]Foreign room: animals in cage were displaced from the original room to a novel room
[17]Strobe light: the animal is exposed to a video of strobe light played using electronic devices
[18]Water deprivation: water bottle was removed from the cage to restrict rats from water access

8.4 Behavioral Assessment

All rats were subjected to behavioral assessment after the 28-day chronic mild stress intervention. The behavioral assessment assessed include Morris water maze (MWM), Elevated plus maze (EPM), T-Maze, Forced swim test (FST), open field test (OFT) and Object Recognition. All experiments were performed in a quiet and darkened room illuminated only by sparse light.

the escape, escape latency (seconds) is expressed as mean±standard of mean from six replicates (n=6) per group.

8.4.2 Elevated Plus Maze (EPM)

Equipment Setup

The elevated plus maze (EPM) consists of four arms, two open arms without walls and two enclosed walls of 40 cm high, 50 cm long and 15 cm wide. Each arm of the maze is attached with firm metallic legs with 70 cm high. The EPM was placed in a room with bright lighting, close to the center of the room. The levels of illumination of both open and closed arms were maintained similar. A video camera was set up above the elevated plus maze to capture and record the animal's behavior.

Assessment

Animal was taken out from its cage and placed at the middle (ie. the junction of the open and closed arm) of EPM, facing away from the maze towards the wall. Each animal was given 5 minutes to explore freely on the EPM. Throughout the assessment, the EPM was cleaned and dried with 70% ethanol before accessing the next animal. The number of open arm entries and time spent in open arms were observed, timed and recorded. The number of entries to open arms and the duration spent on open arms were recorded and expressed as mean±standard of means from six replicates (n=6) per group.

8.4.3 Forced Swim Test

Equipment Setup

Forced swim test (FST) was performed in a black opaque swim cylinder with a depth of 68 cm and diameter of 40 cm. The cylinder was filled up with water to the depth of 30 cm, leaving some space on top to prevent the escape of rat. A video camera was set up above the swim cylinder to capture and record the animals' behavior during the test.

Assessment

Each animal was gently placed into the water in the swim cylinder and was given 5 minutes to swim freely in the swim cylinder. The behavior of the animals were observed and recorded throughout the test. All rats were dried thoroughly with clean towel after the FST before returning them to their respective cage throughout the assessment. The duration of immobility of the rats were timed and then expressed as mean±standard of mean from six replicates (n=6) per group.

8.4.4 Open Field Test

Equipment Setup

Open field test was performed using an opaque rectangular box with the dimension of 32 cm high, 38 cm width and 52 cm long was placed in the center of the experiment room supplied with bright lighting. A video camera was set up above the rectangular box to capture the behavior of the animals.

Assessment

Each animal was gently transferred from its cage into the OFT and allowed to freely explore inside the box. Duration of exploratory and immobility were observed in rats during 5 min open field test. The box was cleaned with 70% ethanol during the interval of each test throughout the assessment. The duration of exploratory and immobility was expressed as mean±standard of mean from six replicates (n=6) per group.

8.4.5 Novel Object Recognition Test

Equipment Setup and Assessment

Novel Object Recognition Test was performed in an opaque rectangular box with the dimension of 32 cm high, 38 cm width and 52 cm long and was placed in the center of the experimental room. This behavioral assessment involved 2 phases, namely familiarization phase and test phase. During the familiarization phase, two identical objects (identical in shape, size and weight) were placed into the rectangular box. Each animal was placed in the rectangular box and was given 2 minutes to explore freely in it. Whereas during the test phase, one of the old object was replaced by a novel object (similar in weight and size) with shape. Similarly, each animal was placed in the rectangular box and was given 2 minutes to explore freely in it. A video camera was set up above the rectangular box throughout the experiment to capture the behavior of the animals in both phases. The box was cleaned with liquid soap, water and dried during the interval of each test. The interval given between the familiarization phase and the test phase was one hour. Time spent to explore the novel object is expressed as discrimination index following the equation below:

Descrimination index=(Time spent on novel object)/ (Total time spent on old+novel object)×100% (Cogn Process,2012,13(2):93-110)

The data was expressed as mean±standard of mean from six replicates (n=6) per group.

8.4.6 Statistical Analysis

All data were analysed statistically by IBM SPSS Statistics 20.0 (IBM Co., Armonk, N.Y., USA). One-way analysis of variance was carried out to analyze the statistical difference between group means. The statistical level of significance was set at $\alpha=0.05$, and the multiple means comparison was assessed by Tukey's test. All data presented as the mean values of three independent experiments (n=6) unless stated otherwise.

8.5 Blood Collection and Organ Extraction

At the end of the experiments, blood samples were collected via cardiac puncture, and transferred into EDTA-coated tubes, immediately after the rats were sacrificed using carbon dioxide asphyxiation. Shortly after blood collection, brain was removed following decapitation. Brain tissue samples used for ELISA and hydrogen peroxide analysis were kept in ice-cold PBS.

8.5.1 Biochemical Analysis

Homogenization of Brain Samples

The extracted rat's brain stored in 1× phosphate buffered saline (pH 7.4) in 4° C. was processed immediately after the dissection. The brain tissue samples were sectioned into 3 regions (cerebellum, cerebrum and hippocampus). The sectioned brain tissue samples were then homogenized at 70-100 Hz for 10 minutes under cold ice condition. All homogenized samples were stored at −20° C. prior to use.

Blood Samples

The blood collected in anticoagulant EDTA tube was incubated at room temperature for 10-20 minutes before being centrifuged at 3000 rpm for 20 minutes. The supernatant was collected as plasma samples and stored in 1.5 ml micro centrifuge tubes, kept at 4° c. for immediate analysis. Extra plasma samples were kept at −20° C. prior to use.

Enzyme-Linked Immunosorbent Assay (ELISA)

Enzyme-linked immunosorbent assay (ELISA) was performed to quantify several cytokines, key neurotransmitters and biomarkers associated with neurogenesis. ELISA was performed according to the manufacturer's instructions (R&D System Inc, USA).

Briefly, 10 µl homogenized brain tissues or plasma were loaded at onto the bottom of the wells without touching the well wall. 40 µl of sample dilution buffer is added to dilute the samples. The diluted samples were incubated for 30 minutes at 37° C. Thereafter, the samples were discarded and washed five times with washing buffer provided. Subsequently, 50 µl of the Horseradish Peroxidase (HRP)-conjugated antibody was added to each well. The mixture was incubated for another 30 minutes at 37° C. Then, mixture was discarded and washed five times with washing buffer provided. Subsequently, 50 µl chromogen solution A and 50 µl chromogen solution B were added to each well and mixed with gentle shaking. The mixture was then incubated for 15 minutes at 37° C. Light exposure was avoided during this step. Next, 50 µl of stop solution was added to each well to terminate the reaction. Lastly, absorbance O.D. at 450 nm was read using Thermo Multiskan-GO ELISA plate reader. Standard curve is generated using same procedure as mentioned above.

Hydrogen Peroxide (H2O2) Measurement in Brain

Hydrogen peroxide levels in brain homogenate samples were evaluated using Amplex Red assay kit (Molecular Probes Inc., Eugene, Oreg., USA) according to manufacturer's protocol.

9.0 Identification of Protein from *L. fermentum* PS150

Following all these positive findings, the protein fraction of *L. fermentum* PS150 was isolated and further identified. The protein fraction was pre-purified by ammonium sulphate precipitation and was then recovered on a three-step chromatography procedure.

9.1 Protein Extraction

Crude protein fraction was extracted as described previously (8.1.2). The crude protein fraction was then desalted using 75% acetone and remove salts by centrifugation (7000 g, 30 min, 4° C.), repeated for three times. Pellet collected was dissolved in deionized water. Protein content was estimated using the Bradford assay (Bio-Rad, Hercules, Calif., USA) using BSA as standard.

9.2 Gel Free Fractionation

Proteins were separated into multiple fractions based on molecular mass using a GELFREE™ 8100 Fractionation System (Expedeon, San Diego, Calif., USA) containing preformulated HEPES running buffer and Tris Acetate sample buffer (AMR Incorporated) according to manufacturer's instructions. *L. fermentum* PS150 proteins were dissolved in sample buffer and loaded into individual loading chambers of a 5% Tris-Acetate cartridge designed to separate proteins in the mass range of 60-300 kDa. The instrument was automatically paused at predefined intervals and the liquid fraction removed with a pipette. The sequence was then restarted and the process continued to collect the next size-based fraction. This process was repeated until all fractions were collected.

After recovery of 12 individual fractions, the fractions were collected and washed twice using acetone and subjected to vacuum concentrator to remove acetone. Each individual fraction was standardized to same protein content (2.0 µg/mL) and tested in cell culture treatment using the previous method stated in 7.3.

9.3. 1DE Gel Analysis

To estimate the molecular size of each individual protein fraction, once after recovery of 12 individual fractions from GELFREE™ 8100 Fractionation System, standard 1DE was performed using 10% SDS-PAGE (Bio-Rad). Protein separation was carried out for 80 min at 110 V in Tris/glycine/SDS running buffer (Bio-Rad) using Criterion electrophoresis equipment (Bio-Rad). Proteins in the gels were stained using Coomassie Brilliant Blue protein gel stain (Molecular Probes, Eugene, Oreg., USA) and protein bands were visualized using a ChemiDoc XRS Camera and Quantity One 1D analysis software (Bio-Rad).

9.4 Reversed-Phase High Performance Liquid Chromatography (RP-HPLC)

The final purification step of the protein fraction by reversed-phase high performance liquid chromatography (RP-HPLC) on HiTrap Q HP column. Elution was performed at a flow rate of 0.8 mL/min with Solvent A (25 mM Tris HCl) for 10 min. Then, a linear gradient from 0% to 100% solvent B (25 mM Tris HCl containing 1 M NaCl) was performed in 70 min. The eluted peaks were individually collected and checked for neuroprotective activity against dexamethasone as described (7.3).

9.5 Identification of Protein Fraction by Orbitrap LC/MS

Peptide identifications were accomplished at the Institutional Centre for Advanced Analytical Toxicology Services, Universiti Sains Malaysia. Fraction of interest from RP-HPLC (0.2 mg) was solubilized in denaturing buffer (6M guanidine-HCl/25 mM ammonium bicarbonate, pH 8.5) and 1 mg/ml DTT/25 mM Ammonium bicarbonate (prepared freshly) was then added to the protein solution and incubated at 55° C. for 30 minutes. Followed by addition of 1 mg/mL iodoacetamide/25 mM ammonium bicarbonate (prepared freshly), then covered with aluminium foil and incubated at 55° C. for 15 minutes. The reduced and alkylated protein sample was then buffer exchanged with 25 mM ammonium bicarbonate using spin-column with molecular cut-off of 15 kDa for 3 times (30 min each time). Trypsin was then added to the sample and incubated at 37° C. for 18 h. The sample was added with formic acid before subjected to freeze-drying. Sample was subjected to MALDI-TOF mass spectrometry analysis and the mass peaks were identified. All possible fragments were generated and their corresponding molecular weights and peptide sequences were identified. Subsequently, data analysis was performed using PEAKS studio version 6.0 and the selection of potential bioactive peptide sequences was carried out using the database of functional annotation for all proteins encoded in the genome of *L. fermentum* PS150.

9.6 Docking Simulation

The 3D model of the elongation factor to (EF-Tu) of *L. fermentum* PS150 was built using Swiss-MODEL (Schwede 2003). The EF-Tu from *Thermus thermophiles* (PDB ID: 2C77) was used as a template due to two reasons 1) there were no available *lactobacillus* derived EF-Tu crystal structure in Protein Data Bank (PDB) and 2) the *T. thermophiles* derived EF-Tu showed the highest sequence identity (74.81%) to EF-Tu of *L. fermentum* PS150 in the database. Crystal structure of Interferon-γ (IFNγ) and Interferon-γ receptor (IFNγR; PDB ID: 1FYH; resolution of 2.04 A) were obtained from the Protein Data Bank (PDB). In addition IFNγ39 (a synthetic peptide derived from the first 39 amino acids of IFNγ known to inhibit IFNγR reactivity) were also derived from the crystal structure of IFNγ to serve as a positive control in this study.

Molecular Docking IFNγ to IFNγ Receptor

All water molecules and ligand were removed prior to the Cluspro 2.0:protein-protein docking job submission. In the Cluspro 2.0:protein-protein docking (Antibody mode), IFNγ and IFNγR was submitted as ligand and receptor respectively. All the conformation generated were further analysed with BIOVIA Discovery Studio 4.5 (Humphrey et al. 1996) to evaluate their root-mean square deviation (RMSD) value. The conformation with the lowest binding free energy, lowest RMSD value and most populated cluster was used as a benchmark control for comparison in further analysis. Ligplot+v1.4.5 (Laskowski and Swindells, 2011) were used to visualize the interactions between IFNγ and the interacting residues on IFNγR (TYR49, TRP82, GLU101, HIS205, VAL206 and TRP207; Randal and Kossiakoff, 2001) of the selected conformation.

Molecular Docking—IFNγ39 to IFNγ Receptor

All water molecules and ligand were removed prior to the Cluspro 2.0:protein-protein docking job submission (Kozakov et al., 2013). In the Cluspro 2.0:protein-protein docking (Antibody mode), IFNγ39 and IFNγR was submitted as ligand and receptor respectively. The conformation with the lowest binding free energy and most populated cluster was used to make comparison with benchmark control as previously completed. Ligplot+v1.4.5 (Laskowski and Swindells, 2011) were used to visualize the interactions between IFNγ39 and the interacting residues on IFNγR (TYR49, TRP82, GLU101, HIS205, VAL206 and TRP207; Randal and Kossiakoff, 2001) of the selected conformation.

Molecular Docking—EF-Tu to IFNγ Receptor

All water molecules and ligand were removed prior to the Cluspro 2.0:protein-protein docking job submission. In the Cluspro 2.0:protein-protein docking (Antibody mode), EF-Tu and IFNγR was submitted as ligand and receptor respectively. The conformation with the lowest binding free energy and most populated cluster was used to make comparison with benchmark control as previously completed. Ligplot+ v1.4.5 (Laskowski and Swindells, 2011, J. Chem. Inf. Model, 51: 2778-2786) were used to visualized the interactions between EF-Tu and the interacting residues on IFNγR (TYR49, TRP82, GLU101, HIS205, VAL206 and TRP207 of the selected conformation.

Example 1 Identification of *L. fermentum* P S150 and General Genomic Features of the Chromosome Sugar utilization for PS150 used in the present invention was investigated using API 50 CHL kit (bioMerieux, France), and the results are shown in Table 2. The fermentation test indicates that PS150 harbor a biochemical property similar to *Lactobacillus fermentum*.

TABLE 2

Results of Fermentation Test[a]

| carbohydrates substrate | PS150 |
| --- | --- |
| CONTROL | − |
| Glycerol | − |
| Erythritol | − |
| D-Arabinose | − |
| L-Arabinose | − |
| D-Ribose | + |
| D-Xylose | − |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |
| L-Sorbose | − |
| L-Rhamnose | − |
| Dulcitol | − |
| Inositol | − |
| D-Mannitol | − |
| D-Sorbitol | − |
| Methyl-α-D-mannopyranoside | − |
| Methyl-α-D-glucopyranoside | − |
| N-Acetyl glucosamine | − |
| Amygdalin | − |
| Arbutin | − |
| Esculin ferric citrate | − |
| Salicin | − |
| D-Cellobiose | − |
| D-Maltose | + |
| D-Lactose (bovine origin) | + |
| D-Melibiose | + |
| D-Saccharose (sucrose) | + |
| D-Trehalose | + |
| Inulin | − |
| D-Melezitose | − |
| D-Raffinose | + |
| Amidon (starch) | − |
| Glycogen | − |
| Xylitol | − |
| Gentiobiose | − |
| D-Turanose | − |
| D-Lyxose | − |
| D-Tagatose | − |

TABLE 2-continued

Results of Fermentation Test[a]

| carbohydrates substrate | PS150 |
| --- | --- |
| D-Fucose | − |
| L-Fucose | − |
| D-Arabitol | − |
| L-Arabitol | − |
| Potassium gluconate | + |
| Potassium 2-ketogluconate | − |
| Potassium 5-ketogluconate | − |

[a]+, positive; −, negative

*L. fermentum* PS150 was cultured in specific artificial culture medium. 16S rRNA and pheS genes from *L. fermentum* PS150 were analyzed by direct sequencing of PCR-amplified DNA fragments. Genomic DNA extraction, PCR mediated amplification of the 16S rDNA and pheS DNA, purification of the PCR product, and sequencing of the purified PCR product were carried out using methods known in the art.

16S rDNA sequence of *L. fermentum* PS150
(SEQ ID NO: 5)
TCAGGATGAACGCCGGCGGTGTGCCTAATACATGCAAGTCGAACGCGT

TGGCCCAATTGATTGATGGTGCTTGCACCTGATTGATTTTGGTCGCCA

ACGAGTGGCGGACGGGTGAGTAACACGTAGGTAACCTGCCCAGAAGCG

GGGGACAACATTTGGAAACAGATGCTAATACCGCATAACAACGTTGTT

CGCATGAACAACGCTTAAAAGATGGCTTCTCGCTATCACTTCTGGATG

GACCTGCGGTGCATTAGCTTGTTGGTGGGGTAACGGCCTACCAAGGCG

ATGATGCATAGCCGAGTTGAGAGACTGATCGGCCACAATGGGACTGAG

ACACGGCCCATACTCCTACGGGAGGCAGCAGTAGGGAATCTTCCACAA

TGGGCGCAAGCCTGATGGAGCAACACCGCGTGAGTGAAGAAGGGTTTC

GGCTCGTAAAGCTCTGTTGTTAAAGAAGAACACGTATGAGAGTAACTG

TTCATACGTTGACGGTATTTAACCAGAAAGTCACGGCTAACTACGTGC

CAGCAGCCGCGGTAATACGTAGGTGGCAAGCGTTATCCGGATTTATTG

GGCGTAAAGAGAGTGCAGGCGGTTTTCTAAGTCTGATGTGAAAGCCTT

CGGCTTAACCGGAGAAGTGCATCGGAAACTGGATAACTTGAGTGCAGA

AGAGGGTAGTGGAACTCCATGTGTAGCGGTGGAATGCGTAGATATATG

GAAGAACACCAGTGGCGAAGGCGGCTACCTGGTCTGCAACTGACGCTG

AGACTCGAAAGCATGGGTAGCGAACAGGATTAGATACCCTGGTAGTCC

ATGCCGTAAACGATGAGTGCTAGGTGTTGGAGGGTTTCCGCCCTTCAG

TGCCGGAGCTAACGCATTAAGCACTCCGCCTGGGGAGTACGACCGCAA

GGTTGAAACTCAAAGGAATTGACGGGGGCCCGCACAAGCGGTGGAGCA

TGTGGTTTAATTCGAAGCTACGCGAAGAACCTTACCAGGTCTTGACAT

CTTGCGCCAACCCTAGAGATAGGGCGTTTCCTTCGGGAACGCAATGAC

AGGTGGTGCATGGTCGTCGTCAGCTCGTGTCGTGAGATGTTGGGTTAA

GTCCCGCAACGAGCGCAACCCTTGTTACTAGTTGCCAGCATTAAGTTG

GGCACTCTAGTGAGACTGCCGGTGACAAACCGGAGGAAGGTGGGGACG

ACGTCAGATCATCATGCCCCTTATGACCTGGGCTACACACGTGCTACA

-continued
ATGGACGGTACAACGAGTCGCGAACTCGCGAGGGCAAGCAAATCTCTT

AAAACCGTTCTCAGTTCGGACTGCAGGCTGCAACTCGCCTGCACGAAG

TCGGAATCGCTAGTAATCGCGGATCAGCATGCCGCGGTGAATACGTTC

CCGGGCCTTGTACACACCGCCCGTCACACCATGAGAGTTTGTAACACC

CAAAGTCGGTGGGGTAACCTTTTAGGAGCCAGCCGCCTAAGGTGGGAC

AGATGATTAGGGTGAAGTCGTAACAAGGTAGCCGTAGGAGAACCTGCG

GTTG pheS gene sequence
(SEQ ID NO: 6)
AAGACACCTTCTACGTGACCCCGTCTGTTTTGATGCGGACCCAAACGT

CGCCAATGCAGGCCCGGATGCTGGAACAACACGACTTCTCCAAGGGGC

CGTTGAAGATGATCTCACCGGGGAAGGTTTACCGCCGCGACACCGATG

ACGCTACCCACAGCCACCAATTCCACCAGGTTGAAGGAATCGTGGTCG

GTGAACACGTCACGATGGCAGATTTAAAGGGGACCCTAGAGGCAGTGG

CCCAAAACCTGTTTGGCGACCAGCTCAAGGTGCGTCTGCGCCCGAGTT

ACTTCCCGTTCACGGAACCGTCCGTCGAGGCCGACATCACTTGCTTTA

ATTGCCTGGGGGCCGGTTGCTCAATCTGTAAGGGGACTGGTTGGATCG

AGGTGTTGGGGGCCGGC

The resulting sequence was put into the alignment software provided online by the National Center for Biotechnology Information (NCBI) (http://www.ncbi.nlm.nih.gov/), aligned manually and compared with representative 16S rDNA sequences of organisms. For comparison, 16S rDNA sequences were also obtained from the database provided online by the NCBI. As a result of this analysis, the following Error! Reference source not found. 3 lists those organisms whose 16S rDNA sequences show the highest similarity values compared to the 16S rDNA sequence of *L. fermentum* PS150.

TABLE 3

Organisms whose 16S rDNA sequences show the highest similarity values compared to the 16S rDNA sequence of *L. fermentum* PS150

| Species | Strain No. | Accession number | Similarity(%) |
|---|---|---|---|
| Lactobacillus fermentum | ATCC 14931T | M58819 | 99.60 |
| Lactobacillus equigenerosi | NRIC 0697T | AB288050 | 95.90 |
| Lactobacillus ingluviei | KR3T | AF333975 | 95.86 |
| Lactobacillus gastricus | Kx156A7T | AY253658 | 95.83 |
| Lactobacillus mucosae | CCUG 43179T | AF126738 | 95.19 |
| Lactobacillus coleohominis | DSM 14060T | AM113776 | 93.56 |
| Lactobacillus secaliphilus | TMW 1.1309T | AM279150 | 93.48 |
| Lactobacillus vaginalis | NCTC 12197T | X61136 | 93.08 |
| Lactobacillus pontis | LMG 14187T | AJ422032 | 92.94 |
| Lactobacillus frumenti | TMW 1.666T | AJ250074 | 92.12 |
| Lactobacillus panis | DSM 6035T | X94230 | 92.07 |
| Lactobacillus oris | DSM 4864T | X94229 | 91.78 |
| Lactobacillus euteri | DSM 20016T | L23507 | 91.78 |
| Lactobacillus antri | Kx146A4T | AY253659 | 91.56 |

The *L. fermentum* PS150 has a circular chromosome of 2,238,401 bp and its GC content is 51%. A total of 2,281 genes were predicted, which was made up of 2,206 protein coding genes, 59 tRNAs, 15 rRNAs and one tmRNA (Table 4). In addition, two clustered regularly-interspaced short palindromic repeats (CRISPR) regions were found, which may provide immunity against foreign genetic elements. Of the 2,206 protein coding genes, 465 were predicted as hypothetical proteins with no functions ascribed to them. Based on Clusters of Orthologous Group (COG) functional categorization, 2005 protein coding genes (i.e. 91% of all predicted coding sequence (CDS)) could be assigned to COG functional categories. Of the 2005 protein coding genes, 62% of them belonged to five major COG categories: 447 CDS in category S (function unknown), 364 CDS in category L (replication, recombination and repair), 162 CDS in category E (amino acid transport and metabolism), 140 CDS in category J (translation, ribosomal structure and biogenesis) and 136 CDS in category K (transcription). Moreover there were nine prophage regions identified and interestingly, four of them were predicted as intact prophages. Searches for antibiotic resistance genes revealed six candidate resistance genes that include 30S ribosomal protein S12, maltose O-acetyltransferase, galactoside O-acetyltransferase, putative acetyltransferase, chloramphenicol acetyltransferase and thymidylate synthase.

TABLE 4

A list of predicted genomic features of *L. fermentum* PS150.

| Features | Count |
|---|---|
| Gene | 2281 |
| CDS | 2206 |
| tRNA | 59 |
| rRNA | 15 |
| tmRNA | 1 |
| Repeat region (CRISPR) | 2 |
| Hypothetical protein | 465 |
| Prophage region | 9 |

Chromosomes Comparisons with Other *L. fermentum* Strains

Chromosomes comparisons among bacterial strains can reveal genomic features that are unique to certain strains. The chromosome of *L. fermentum* PS150 was compared with complete genomes from another four strains, *Lactobacillus fermentum* 3872, *Lactobacillus fermentum* CECT 5716, *Lactobacillus fermentum* IFO 3956 and *Lactobacillus fermentum* F6. The predicted prophages of *L. fermentum* PS150 were concatenated and included in the comparisons. As expected, the new genome is clear differences such as in the prophage regions.

A search was done to find out the non-overlapping regions between strain 3872 and PS150, which revealed 98 protein-coding sequences as unique to the latter strain. Out of the 98 sequences, 35 of them encode for hypothetical proteins, which means they have unknown functions or perhaps wrongly predicted as genes. The remaining 63 genes have predicted protein products that include three putative glycosyltransferases that are found in a cluster of genes in a span of less than 15 kb.

Example 2 Assay for Alleviation of Anxiety, Depression & Stress

Analyses on rat behavior were carried out after 4 weeks of chronic mild stress protocol. The elevated plus maze is a widely used behavioral assay for rodents and it has been validated to assess the anti-anxiety effects of pharmacological agents and steroid hormones. Elevated plus maze used in the experiment consisted of four arms (two open arms and two closed arms) and elevated at a height of 50 cm from ground. Rats were placed at the junction of the four arms of the maze, facing an open arm, and entries/duration in each arm was recorded for 5 min. An increase in open arm activity (duration and/or entries) reflects anti-anxiety behavior. *L. fermentum* PS150 and protein fraction treated group significantly have more number of entry of rats into open arms compared to the negative control group ($P<0.05$; FIG. 1. (a)) whereas there was insignificant differences between naïve control group, positive control group (antidepressant treated), *L. fermentum* PS150 treated group and protein fraction treated group (FIG. 1. (a)). Furthermore, ratio of time spent on the closed arms to the time spent on the open arms ratio treated with *L. fermentum* PS150 and protein fraction was significantly lower as compared to negative control group ($P<0.05$; FIG. 1. (b)) while insignificant differences were observed among naïve control group, positive control group (antidepressant treated), *L. fermentum* PS150 treated group and protein fraction treated group (FIG. 1. (b)). Results indicate *L. fermentum* PS150 and protein fraction of *L. fermentum* PS150 could normalize the anxiety behavior resulted from chronic mild stress, back to the original non-anxiety states. In addition, *L. fermentum* PS150 and protein fraction group also showed similar anti-anxiety effects with that of alprazolam, indicating similar effects with a commercial antidepressant.

Figure 2:
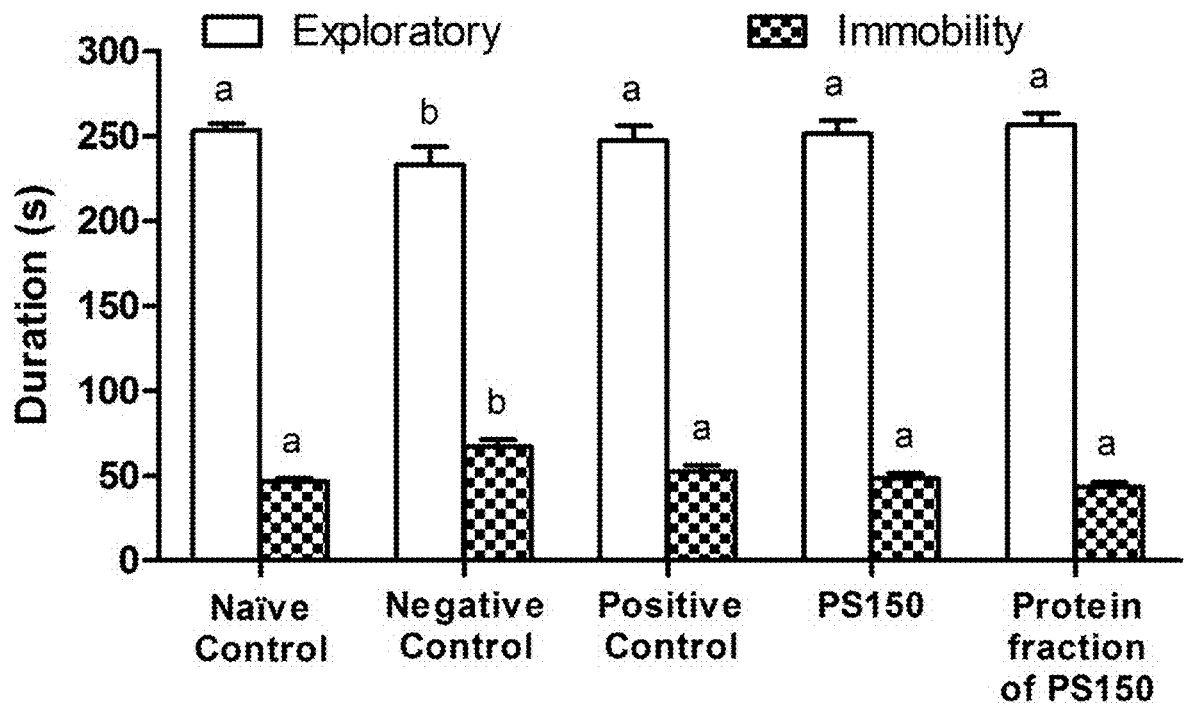
FIG. 2 shows measurement of anxiety related behavior of rats using open field test after 4 weeks of chronic mild stress protocol. Duration of exploratory and immobility observed in rats during 5 min open field test. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{ab}$ A significant difference in the duration of exploratory and immobility of rats between different groups; P<0.05.

The open field test is broadly used to assess exploratory behavior and validated for use in the measurement of anxiety-related behaviors. The procedure consists of subjecting the rat, to an unknown environment from which escape is prevented by surrounding walls. *L. fermentum* PS150 and protein fraction of *L. fermentum* PS150 treated group significantly increased the duration of exploratory activity in rats compared to the negative control group ($P<0.05$; FIG. 2). The exploratory and immobility activity in rats are insignificantly different between naïve control group, positive control group (antidepressant treated), *L. fermentum* PS150 treated group and protein fraction treated group (FIG. 2). Increased exploratory behaviours in rats indicate less anxiety states, whereas immobility indicate anxiety behaviour in rats. Chronic mild stress induced anxiety in rats, but *L. fermentum* PS150 and protein fraction of *L. fermentum* PS150 could normalize the anxiety behavior resulted from chronic mild stress, back to the original non-anxiety states. In addition, *L. fermentum* PS150 and protein fraction group also showed similar anti-anxiety effects with that of alprazolam, indicating similar effects with a commercial antidepressant.

Figure 3:
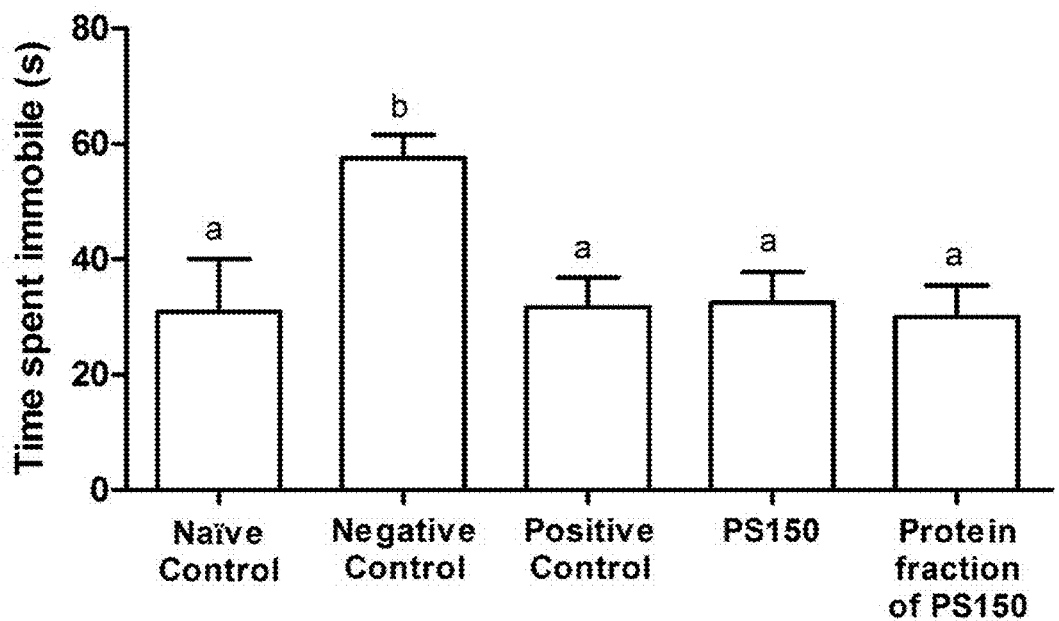
FIG. 3 shows measurement of depressive related behavior observed in rats using forced swim test after 4 weeks of chronic mild stress protocol. Time spent immobile in rats during 5 min forced swim test is recorded. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{ab}$ A significant difference in the time spent immobile of rats between different groups; P<0.05.

Forced swim test is one of the most commonly used assays for the study of depressive-like behavior in rodents. The forced swim test is based on the assumption that when placing an animal in a container filled with water, it will first make efforts to escape but eventually will exhibit immobility that may be considered to reflect a measure of behavioral despair. In forced swim test, a swimming cylinder filled with 30 cm depth of water. Depression assessment of rats was performed by scoring predominant behavior in each 5-s period of the 300-s test. *L. fermentum* PS150 and protein fraction treated group significantly spent less time immobile compared to the negative control group ($P<0.05$; FIG. 3). Time spent immobile in rats are insignificantly different between naïve control group, positive control group (antidepressant treated), *L. fermentum* PS150 and protein fraction treated group (FIG. 3). Similar effect is observed from *L. fermentum* PS150, protein fraction and antidepressant, where depressive-like behavior caused by chronic mild stress was normalized to same level in naïve control. *L. fermentum* PS150 and protein fraction of *L. fermentum* PS150 could normalize the depressive behavior resulted from chronic mild stress, back to the original non-depressed states. In addition, *L. fermentum* PS150 and protein fraction also showed similar anti-depression effects with that of alprazolam, indicating similar effects with a commercial antidepressant.

Figure 4:
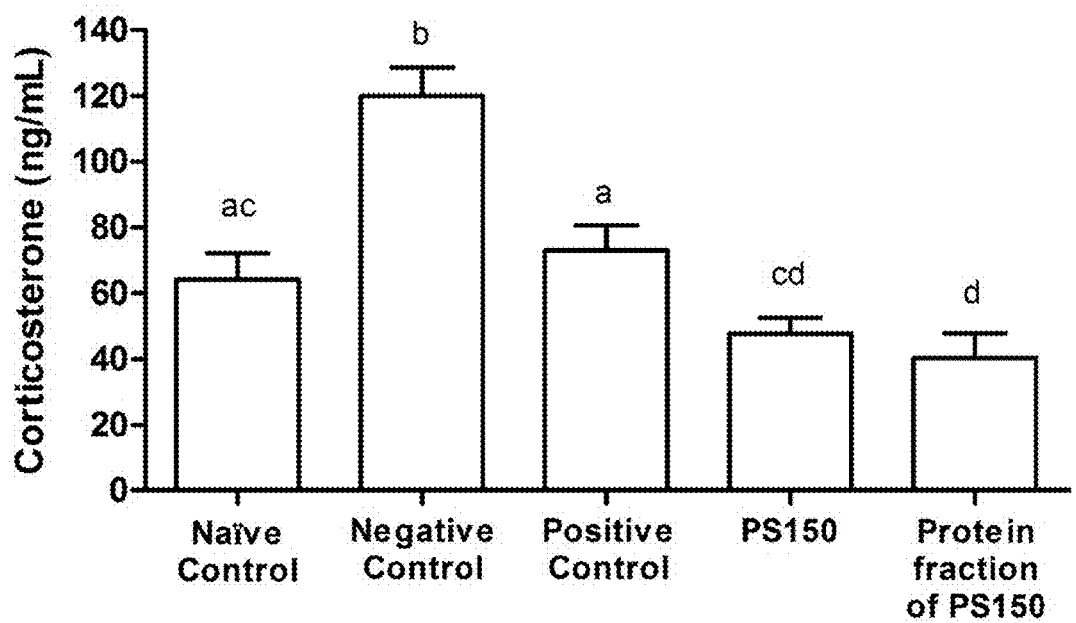
FIG. 4 shows concentration of plasma corticosterone levels observed in rats after 4 weeks of chronic mild stress protocol. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{abcd}$ A significant difference of corticosterone levels of rats between different groups; P<0.05.

Plasma corticosterone level was significantly lower in *L. fermentum* PS150 and protein fraction group as compared to the negative control group and positive control groups ($P<0.05$; FIG. 4). Exposure to repeated or prolonged stressors gives rise to chronic stress. Chronic stress eventually leads to dysregulation of the HPA axis which results in increased plasma corticosterone level. Elevated corticosterone level indicates anxiety and depressive related behavior. Our data showed that *L. fermentum* PS150 and protein fraction of *L. fermentum* PS150 normalized the anxiety, depressive and stress behaviors resulted from chronic mild stress, back to the original non-stressed states, and may even exert a pathological effect better than with that of alprazolam, a commercial antidepressant.

Figure 5:
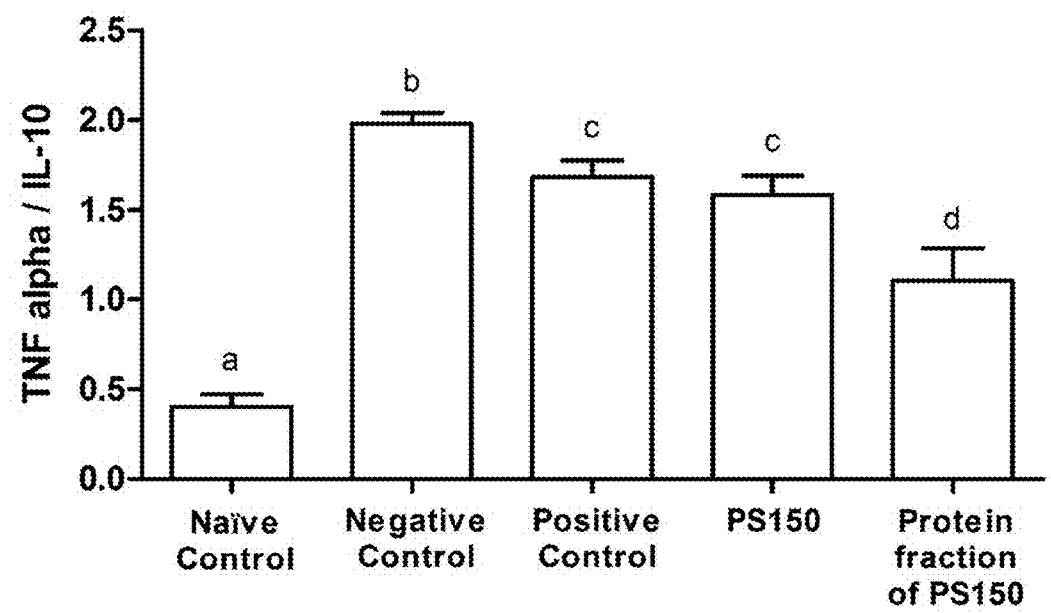
FIG. 5 shows the ratio of plasma TNF alpha and interleukin-10 level in rats after 4 weeks of chronic mild stress protocol. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{abcd}$ A significant difference of the ratio of plasma TNF alpha and interleukin-10 level in rats between different groups; P<0.05.

Ratio of plasma TNF alpha and interleukin-10 was significantly lower in *L. fermentum* PS150 treated group and protein fraction treated group as compared to the negative control group ($P<0.05$; FIG. 5). TNF alpha is pro-inflammatory cytokine while interleukin-10 is anti-inflammatory cytokine. Depressed patients often have higher levels of TNF alpha but lower levels of IL-10 than those who are not depressed, with the TNF alpha: IL-10 ratio correlating significantly with the severity of depressive symptoms. Our present findings suggested *L. fermentum* PS150 and protein fraction of *L. fermentum* PS150 normalized the anxiety, depressive and stress behaviors resulted from chronic mild stress, back to the original non-stressed states, possibly via modulation of cytokines. *L. fermentum* PS150 and protein fraction of *L. fermentum* PS150 also had similar effects as alprazolam, indicating a similar stress reducing effect as a commercial antidepressant.

Example 3 Assay for Improvement of Brain Cognition and Protection of Neuronal Apoptosis It is well documented that stress often impose negative effects on memory and other cognitive functions. In order to assess cognition performance, Morris water maze was used to evaluate memory retention, and the novel object recognition test was used to access the learning and recognition memory.

Figure 6:
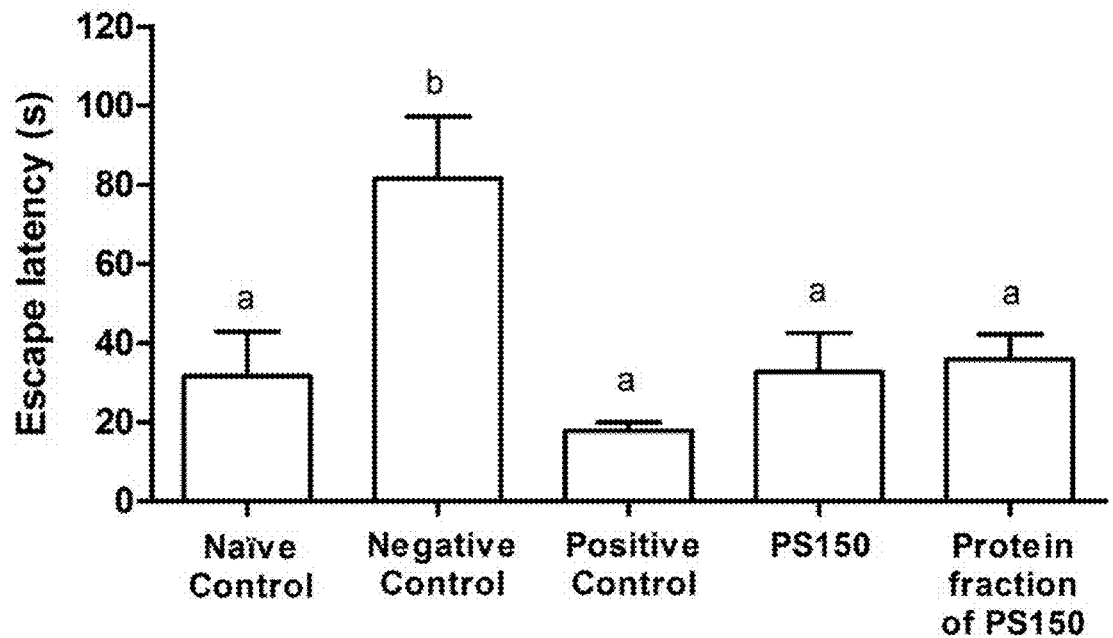
FIGS. 6 (a) and (b) show memory and cognitive function assessment observed in rats using Morris water maze and novel object recognition test after 4 weeks of chronic mild stress protocol; (a) Escape latency of rats in Morris water maze; (b) Discrimination index of rats in novel object recognition test. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{ab}$ A significant difference of the escape latency (a) and discrimination index (b) of rats between different groups; P<0.05.
Figure 6:
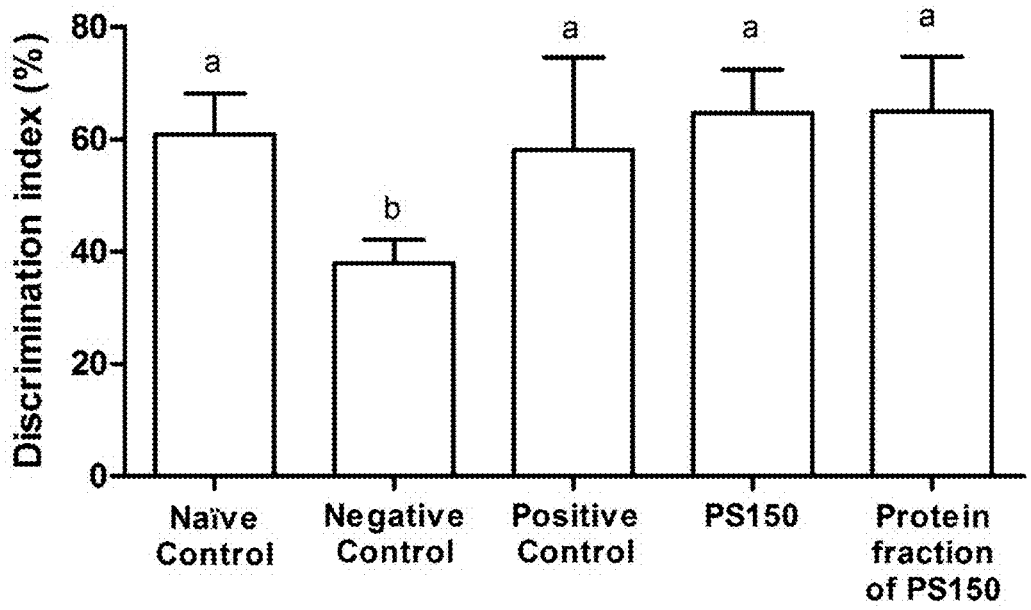

The Morris water maze is a task extensively used and accepted by behavioral physiologist and pharmacologist to assess and compare learning and memory in rodents. Spatial learning, the most basic Morris water maze procedure is used in the experiment. The concept behind it is that the animal must learn to use distal cues to navigate a direct path to the hidden platform when started from different, random locations around the perimeter of the tank. The water maze is 210 cm in diameter and has sides that are 51 cm in height with non-reflective interior surfaces. Escape latency (EL) is the time taken by the animal to move from the starting quadrant to find the hidden platform in the target quadrant. *L. fermentum* PS150 and protein fraction treated group significantly decreased escape latency compared to the negative control group whereas negative control group significantly increased escape latency compared to the other groups (P<0.05; FIG. 6 (*a*)). Insignificant difference was observed between nave control group, positive control group, *L. fermentum* PS150 treated group and protein fraction treated group (FIG. 6 (*a*)). *L. fermentum* PS150 and protein fraction treated group significantly have higher discrimination index in the novel object recognition test (FIG. 6 (*b*)) as compared to the negative control rats, with similar effects to that of the positive control (antidepressant group) and nave control (not stressed) rats (P<0.05). Our present findings indicated that *L. fermentum* PS150 and protein fraction *L. fermentum* PS150 normalized impaired cognitive function resulted from chronic mild stress in rats (significantly better than the negative control group).

Figure 7:
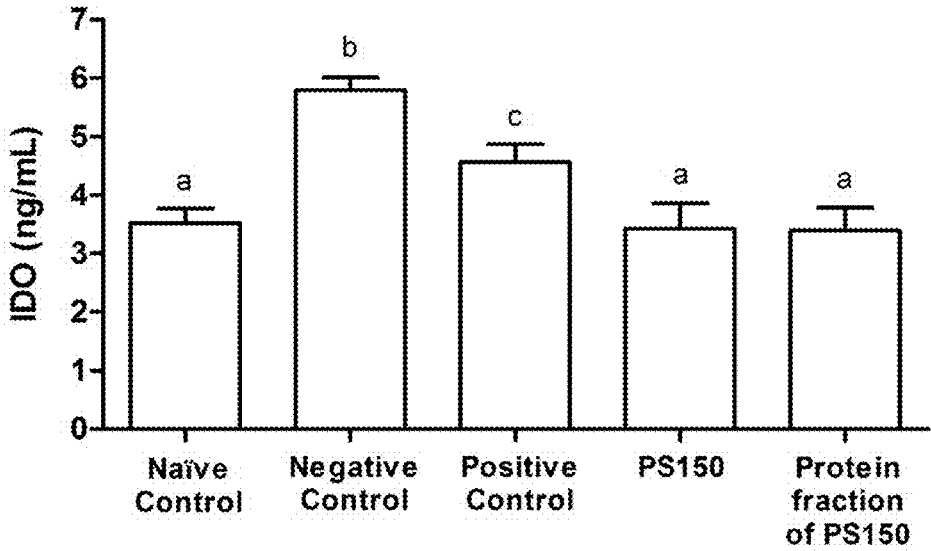
FIGS. 7 (a), (b) and (c) show plasma indoleamine-2,3-dioxygenase (IDO)(a), tryptophan (b) and kynurenine (c) in rats after 4 weeks of chronic mild stress protocol. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=6. $^{abc}$ A significant difference in plasma IDO (a), tryptophan (b), and kynurenine (c) concentration between different groups; P<0.05.
Figure 7:
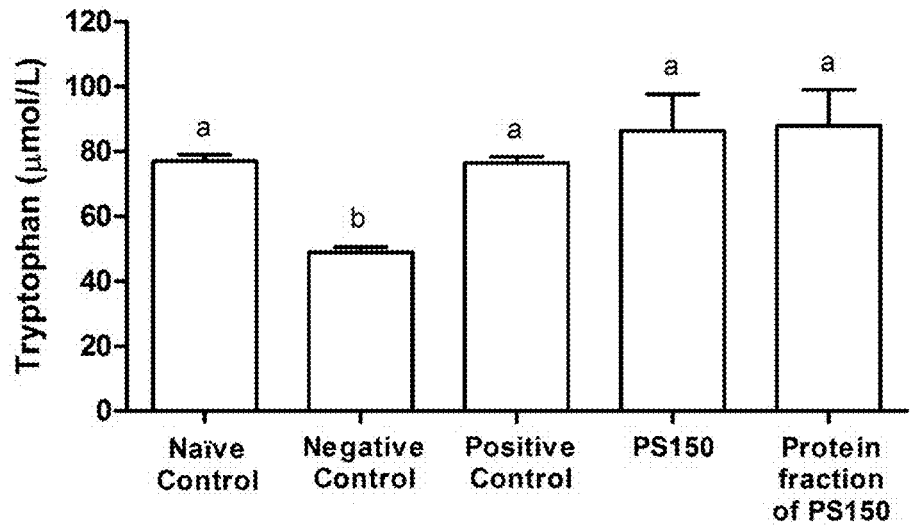
Figure 7:
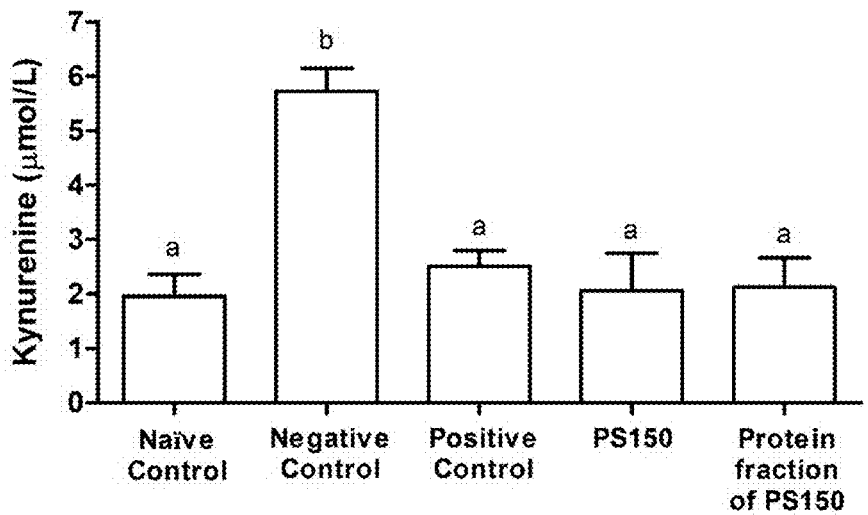

TNF-alpha contribute to the pathogenesis of neurodegenerative diseases by an activation of the hypothalamo-pituitary-adrenocortical (HPA) axis, the stimulation of the indoleamine 2,3-dioxygenase (IDO) which leads to tryptophan depletion, by immunologically mediated destruction of neurons, or neurotoxic release of glutamate. IDO is an enzyme that degrades tryptophan into kynurenine, which is involved in pathophysiology of neurodegenerative diseases. In the event of a lower ratio of plasma TNF alpha and interleukin-10 level in *L. fermentum* PS150 and protein fraction group, a significant reduction in plasma IDO level was also observed as compared to the negative control and positive control (P<0.05; FIG. 7 (*a*)). Given that a lower concentration of plasma IDO was detected in *L. fermentum* PS150 and protein fraction group, a higher level of plasma tryptophan was also observed as compared to the negative control group (P<0.05; FIG. 7 (*b*)). Our data showed less amount of tryptophan being degraded into kynurenine, while plasma kynurenine level was also significantly lower in *L. fermentum* PS150 and protein fraction group as compared to the negative control group (P<0.05; FIG. 7(*c*)). Our present findings indicated that *L. fermentum* PS150 and protein fraction *L. fermentum* PS150: (a) prevented neurodegeneration via reducing the production of kynurenine (significantly better than the negative control group) and (b) restored neurodegeneration back to normal states and was as good as antidepressant (similar effects as the positive control/alprazolam and naïve control groups).

Figure 8:
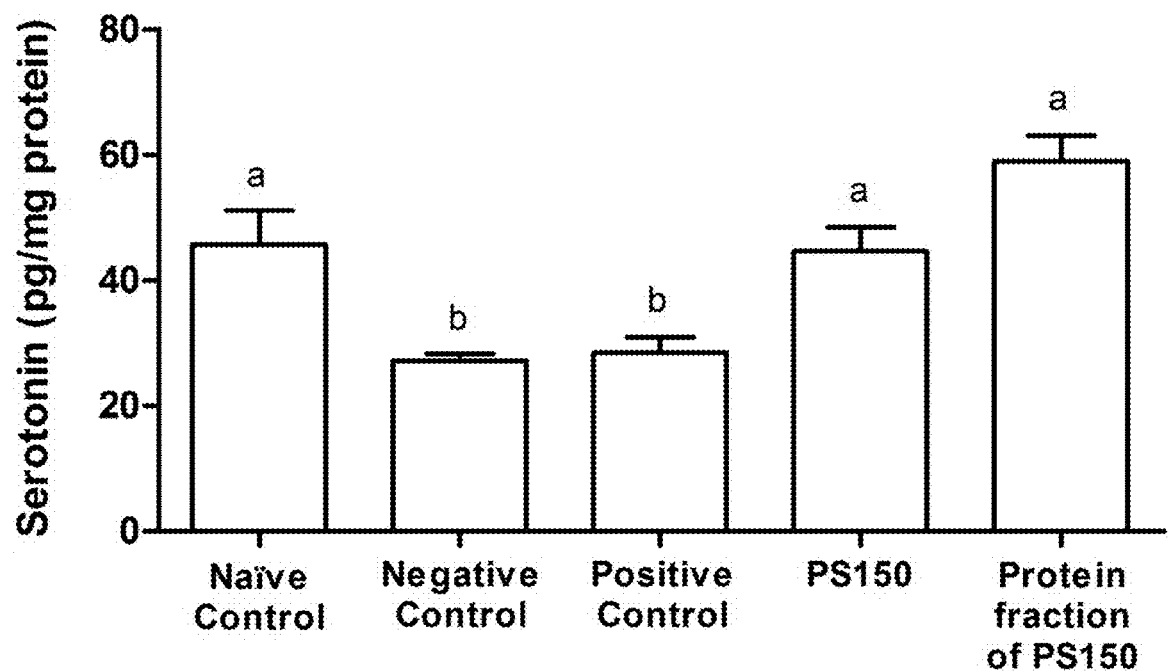
FIG. 8 shows concentration of serotonin in the brain of rats after 4 weeks of chronic mild stress protocol. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=4. $^{ab}$ A significant difference in brain serotonin concentration between different groups; P<0.05.

On the other hand, tryptophan is also the precursor to serotonin. Brain samples were also collected for measurement of serotonin levels. Serotonin is a neurotransmitter involved in transmission of nerve impulses and regulating signals between neurons. Our present findings showed that concentrations of serotonin in the brain was significantly elevated in *L. fermentum* PS150 and protein fraction group as compared to the negative control group (P<0.05; FIG. 8). The result is in tandem with the increased plasma tryptophan level observed in the *L. fermentum* PS150 and protein fraction group. Our present findings indicated that *L. fermentum* PS150 and protein fraction of *L. fermentum* PS150: (a) restored transmission of neurons in the brain that were reduced due to chronic mild stress in rats leading to better cognition (significantly better than the negative control group) and (b) exerted better efficacy than a commercial antidepressant (significantly better than the positive control/ alprazolam group).

Figure 9:
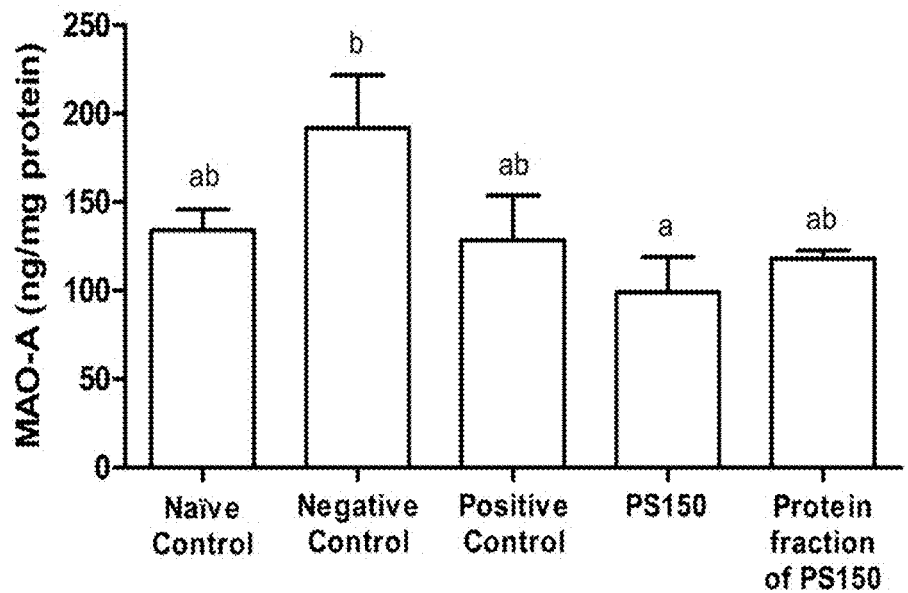
FIGS. 9 (a) and (b) show concentration of monoamine oxidase-A (MAO-A)(a) and hydrogen peroxide (b) in rats whole brain after 4 weeks of chronic mild stress protocol. Naïve control group, where rats were left undisturbed in cage; Negative control, where rats were subjected to chronic mild stress and fed with 200 μL phosphate buffer saline (PBS; pH 7.4); Positive control, where rats were subjected to chronic mild stress and given 200 μL PBS containing 0.045 mg/kg alprazolam; L. fermentum PS150 group, where rats were subjected to chronic mild stress and given 200 μL PBS containing $1 \times 10^9$ cfu viable L. fermentum PS150; Protein fraction of L. fermentum PS150 group, where rats were subjected to chronic mild stress and given 200 μL PBS containing 300 mg/kg protein. Error bars represent standard of means; n=4. $^{ab}$ A significant difference in whole brain MAO-A (a) and hydrogen peroxide (b) concentration between different groups; P<0.05.
Figure 9:
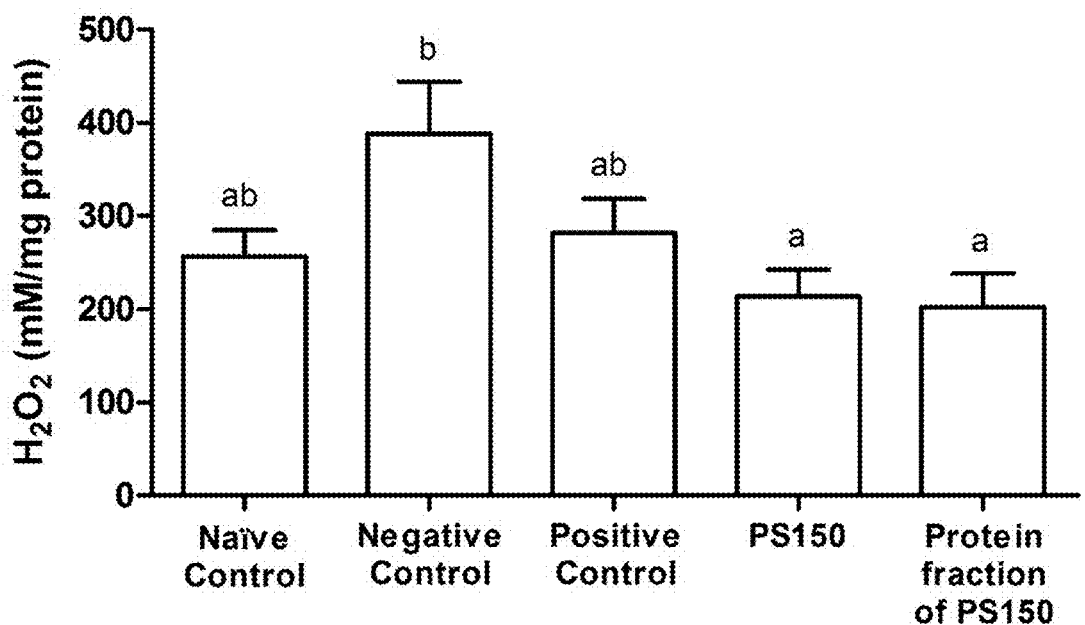

Upon stress, varying apoptotic traits were observed in brains of rats. Monoamine oxidases (MAOs) are mitochondrial enzymes controlling the levels of neurotransmitters in the brain, with MAO-A being functional in apoptosis via activation of caspase-3 and production of reactive oxygen species. Hydrogen peroxide is often detected from apoptotic cells due to its role as a mediator of apoptotic cell death. Upon chronic stress protocol, rats administered with PS150 showed lower brain concentrations of MAO-A (FIG. 9 (*a*)) as compared to the negative control rats (P<0.05). An alleviation of apoptotic traits were evident where a lower brain concentration of hydrogen peroxide was observed in rats administered with PS150 or protein fraction compared to the negative control group (FIG. 9 (*b*), P<0.05).

Both behavioural and brain assessments indicated that PS150 and protein franction of PS150 prevented brain damages in rats caused by chronic mild stress, with the similar potency of a commercial antidepressant, leading to normalized spatial learning, long-term memory, and cognitive functions, and prevent neurodegeneration and neuron apoptosis.

Example 4 Identification of Gene and Protein from *Lactobacillus fermentum* PS150

Figure 10:
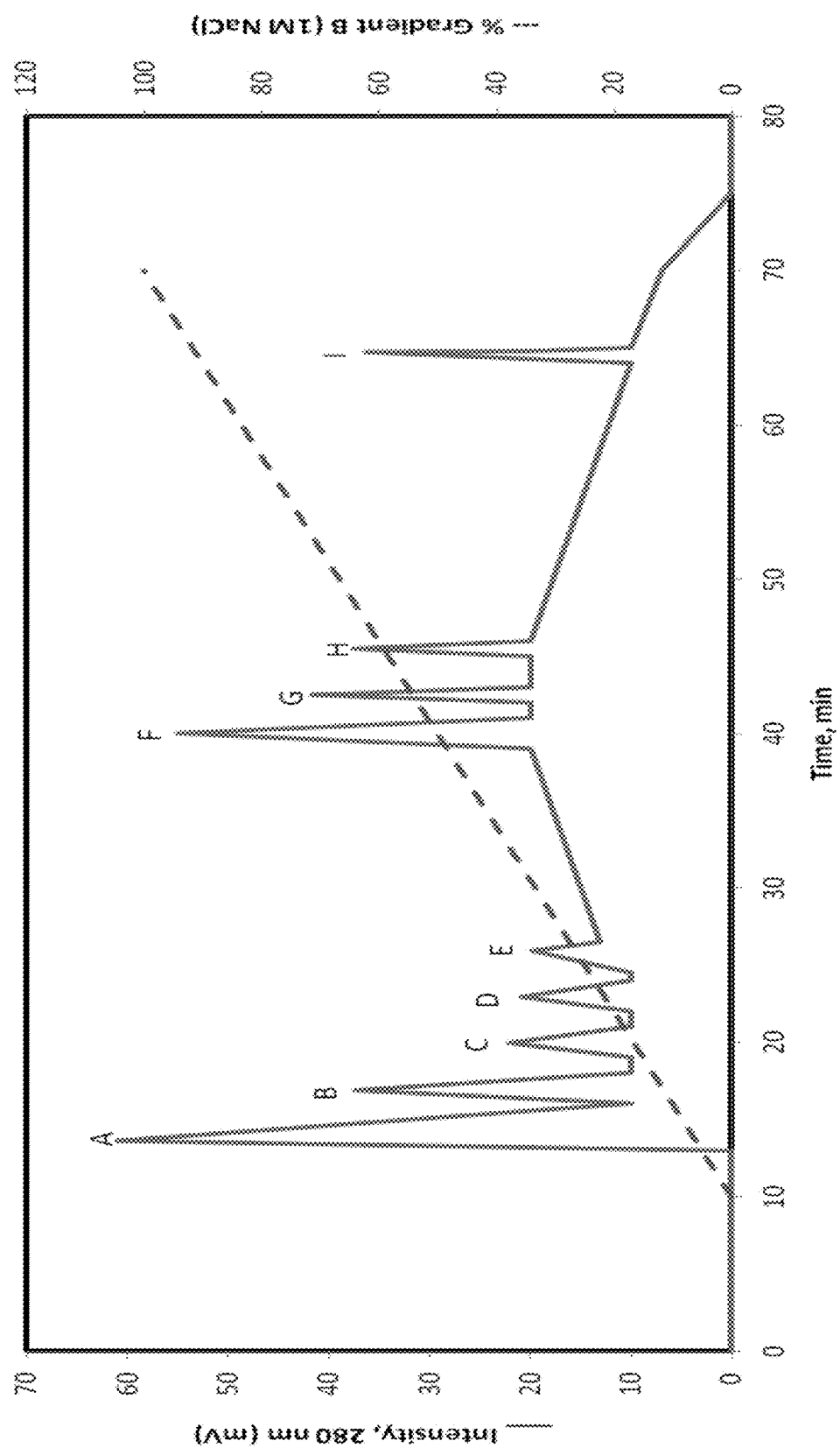
FIG. 10 shows reversed-phase high performance liquid chromatography (RP-HPLC) elution profile of the protein produced by L. fermentum PS150 on an analytical HiTrap Q HP column. Elution was performed at a flow rate of 0.8 mL/min with a linear gradient from 0% to 100% solvent B (25 mM Tris HCl containing 1 M NaCl) in 80 min.

Following all these positive findings, the protein fraction of *L. fermentum* PS150 was further isolated, and identified. The protein fraction was pre-purified by ammonium sulphate precipitation and was then recovered on a three-step chromatography procedure. The final purification step of the protein fraction by reversed-phase high performance liquid chromatography (RP-HPLC) on HiTrap Q HP column revealed the presence of 9 major peaks eluted at 5%, 15% 20%, 25%, 30%, 50%, 55%, 60% and 90% of solvent B (25 mM Tris HCl containing 1 M NaCl) (FIG. 10). The eluted peaks (designated as fractions A, B, C, D, E, F, G, H, and I respectively) were individually collected and checked for neuroprotective activity against dexamethasone.

Figure 11:
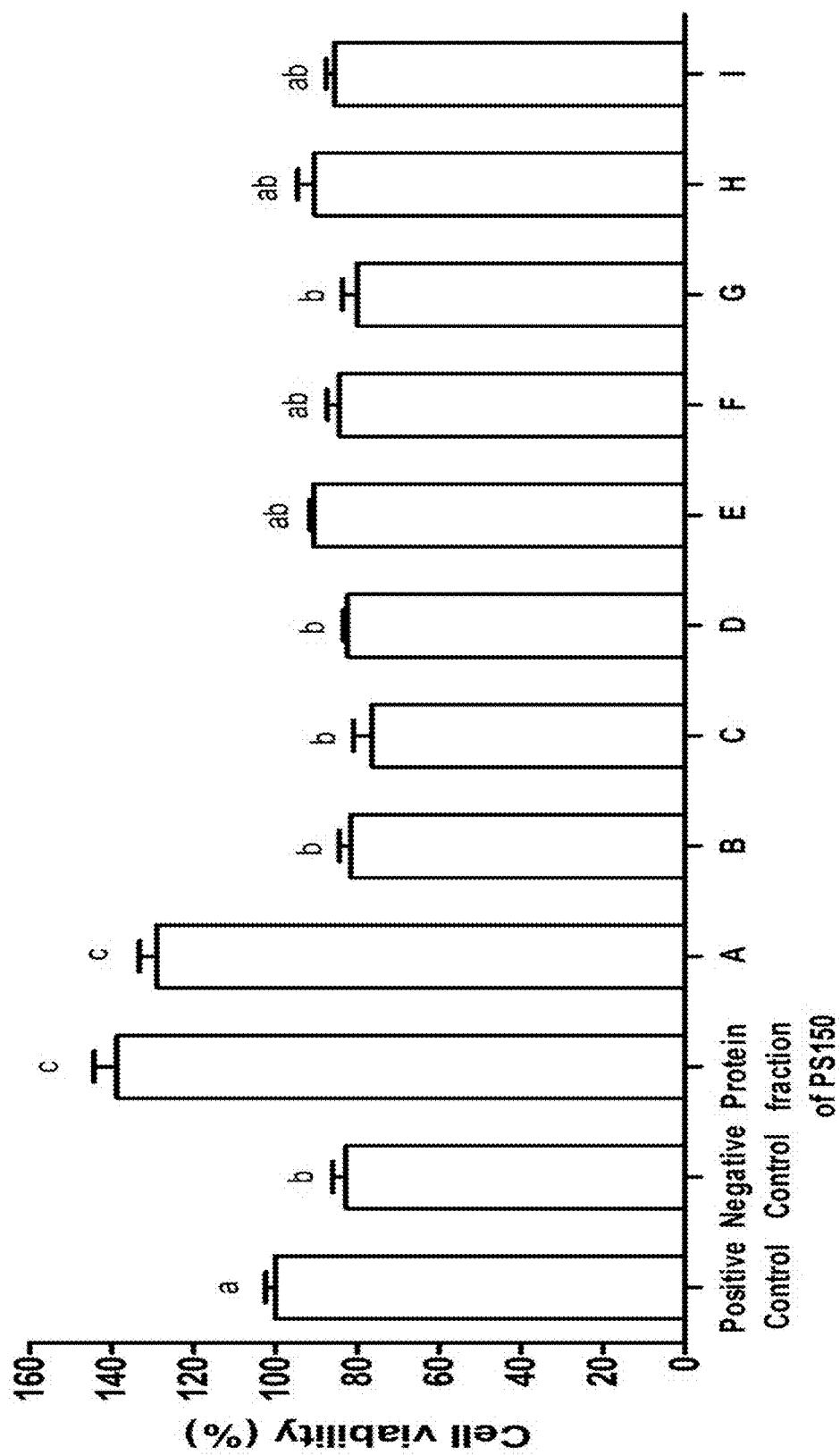
FIG. 11 shows percentage of cell viability upon dexamethasone-induced neurotoxicity in SH-SY5Y neuroblastoma cells. Positive control, where SH-SY5Y cells were treated with unfermented MRS; Negative control, where SH-SY5Y cells were treated with unfermented MRS in the presence of dexamethasone (25 μM); Protein fraction of L. fermentum PS150, where SH-SY5Y cells were treated with protein fraction of L. fermentum PS150 in the presence of dexamethasone (25 μM); Fractions A, B, C, D, E, F, G, H and I, where SH-SY5Y cells were treated with purified protein fractions collected from HPLC. Error bars represent standard of means; n=6. $^{abc}$ A significant difference in percentage of cell viability between different groups; P<0.05.

Apoptosis is a normal physiological programmed cell death that can be enhanced by a variety of external stimuli, such as biomarker of stress, corticosterone. Dexamethasone, a synthetic corticosterone was used to assess the neuroprotective ability of protein faction of *L. fermentum* PS150. Data showed only fraction A has the most prevalent neuroprotective effect (FIG. 11). Positive control cells treated without dexamethasone were taken as 100% viability. Protein fraction of *L. fermentum* PS150 showed significant cytoprotection effect compared to both unfermented medium treated cells, with or without the presence of dexamethasone.

Figure 12:
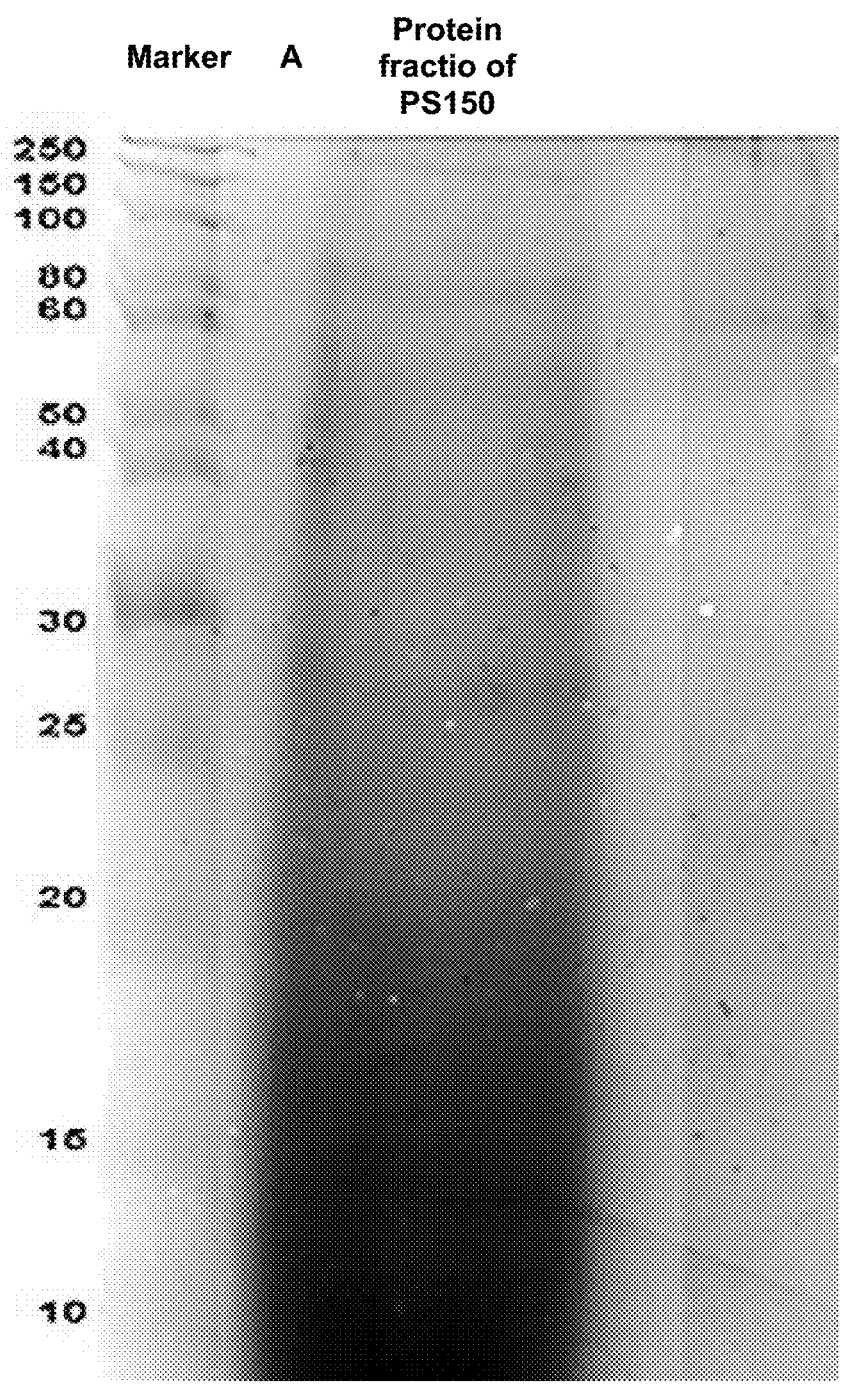
FIG. 12 shows SDS-PAGE gel image of the purified fraction A from the crude protein fraction of L. fermentum PS150. Lane 1: Protein marker; Lane 2: Crude protein fraction of PS150; Lane 3: Purified protein fraction A.

The purified fraction A showed a single band on SDS-PAGE with an estimated molecular weight of approximately 55 kDa (FIG. 12). For protein identification, purified protein collected from HPLC was subjected to MALDI-TOF mass spectrometry analysis. The mass peaks observed over the course of trypsin digestion were identified. All possible fragments were generated and their corresponding molecular weights and peptide sequences were identified. Subsequently, data analysis was performed using PEAKS studio version 6.0 and the selection of potential bioactive peptide sequences was carried out using the database of functional annotation for all proteins encoded in the genome of *L. fermentum* PS150.

With the annotated genome of *L. fermentum* PS150, all the peptide sequences obtained from mass spectrometry was blasted into the nucleotide-translated protein sequence of the bacteria. Among the 150 peptides blasted, only two peptides were found to be identical with the proteins from the bacteria, with both peptide sequence having 100% match to one of the proteins of *L. fermentum* PS150. With this match, the sequence of the protein was determined to be that of SEQ ID NO:4. Such protein was back-translated to nucleotide sequence, with the sequence of SEQ ID NO:7, to obtain its gene sequence.

SEQ ID NO: 7
```
ATGGCAGAAAAAGAACATTATGAACGTACTAAGCCCCACGTTAACATC
GGTACTATTGGCCACGTTGACCACGGGAAGACTACTTTAACCGCAGCT
ATCACCAAGGTATTGGCCGCTAAGGGCCTTGCCAAGGCAGAAGACTAC
TCTGATATCGATGCTGCTCCAGAAGAAAAGGAACGTGGTATCACTATC
AACACTGCCCACGTTGAATACGAAACGGAAAAGCGTCACTACGCTCAC
ATCGACGCTCCAGGGCACGCCGACTACGTTAAGAACATGATCACTGGG
GCCGCTCAAATGGACGGTGCGATCTTAGTTGTTGCCGCAACTGATGGT
CCGATGCCACAAACTCGTGAACACATCCTTCTGGCTCGCCAGGTCGGT
GTTGAATACATCGTTGTCTTCCTTAACAAGACTGACCTTGTTGACGAT
GACGAACTGGTTGACTTAGTTGAAATGGAAGTTCGTGACCTTCTGTCC
GAATACGACTTCCCTGGCGATGATGTTCCGGTTGTTCGTGGGTCCGCT
CTTAAGGCCCTCGAAGGTGACCCAGAACAAGAACAAGTTGTTCTTCAC
CTTCTGGACGTCGTTGACGAATACATCCCAACTCCAAAGCGTCCTACT
GACAAGCCATTCATGATGCCTGTCGAAGACGTCTTCACTATCACTGGT
CGTGGTACTGTTGCTTCTGGTCGTATCGACCGTGGTACTGTTAAGATC
GGTGACGAAGTTGAAATCGTTGGTTTGAAGGAAGACGTTATCAAGTCC
ACTGTTACCGGTGTTGAAATGTTCCACAAGACCCTTGATCTTGGGGAA
GCCGGGGACAACGTCGGTGTCCTTTTACGTGGGGTTTCTCACGACCAA
ATCGAACGTGGTCAAGTTCTGGCAGAACCAGGCTCCATCCAAACGCAC
AAGCAATTCAAGGGTGAAGTCTACGTTATGACCAAGGAAGAAGGGGGC
CGTCACACGCCATTCTTCTCCAACTACCGCCCACAATTCTACTTCCAC
ACTACTGACGTTACTGGTACCATTGAACTCCCAGATGGTGTTGAAATG
GTTATGCCTGGTGACAACGTTACCTTCACTGTTGAACTGCAAAAGCCA
GTTGCCCTTGAAAAGGGTCTGAAGTTCACCATCCGTGAAGGTGGTCAC
ACTGTTGGTGCCGGTGTGGTATCCGAAGTGCTCGACTA
```

This bioactive protein, is identified as an elongation factor Tu, with 396 amino acids residues. Indeed, this molecule is a guanosine nucleotide binding protein that plays a central role in protein synthesis in the cytoplasm. However, the presence of EF-Tu in the different compartments of microorganisms has been well documented. The EF-Tu molecule, originally thought to be restricted to the cytoplasm of bacteria, has been shown to also be associated with the membrane of *E. coli*. Recent studies showed that EF-Tu is an envelope-associated protein that can be released from the cell.

Elongation factor Tu were able to trigger an immunomodulatory response in the rat. In this study, protein fraction treated rats induced anti-inflammatory immune response (reduced the ratio of TNF-alpha and IL-10; P<0.05; FIG. 5). Through reducing TNF-alpha, which contribute to the pathogenesis of neurodegenerative via stimulation of the indoleamine 2,3-dioxygenase (IDO), plasma IDO level is reduced as well (P<0.05; FIG. 7(*a*)). This eventually reduced the turnover rate of tryptophan to kynurenine (P<0.05; FIGS. 7 (*b*) & (*c*)), and lead to increased production of serotonin. The immunomodulatory ability of elongation factor Tu also reduced the plasma corticosterone level which contribute to the alleviation of anxiety, depression and stress.

Altogether, our data proved that this bioactive protein produced by *L. fermentum* PS150 with a sequence as in SEQ ID NO:4 above, is an immunomodulatory compound, supporting our data on alleviation of anxiety, depression and stress in addition to improving cognition, all related to healthier brain functions. We present here, evidences that probiotics bioactive compound such as elongation factor produced by *L. fermentum* PS150 could exert brain health benefits.

Example 5 Protein Variability Analysis of Elongation Factor Tu of *L. fermentum* PS150

Shannon entropy was used to estimate EF-Tu protein variability. In a 21 characters system, H ranges from 0 (i.e. highly conserved, only a single character in the alignment column) to 4.392 (i.e. all 21 characters are equally present). The entropies estimated for the 235 bacteria species and the 25 bacteria species from the *Lactobacillus* genus across the entire protein length with three key domains (GTP EFTU, GTP EFTU D2, and GTP EFTU D3) of the protein.

Highly variable residues are categorized as those that have entropies above the threshold of mean entropy plus two standard deviations. The value of mean plus two standard deviations is used because for most distributions, values larger than it are considered extreme values. Therefore, the first domain GTP EFTU has the most number of variable residues followed by the last domain GTP EFTU D2 and then GTP EFTU D3. Of particular interest are residues that are highly variable when all 235 bacteria species are considered but are not highly variable when only species from the *Lactobacillus* genus are included. Here is a list of residues that meets the mentioned criteria: 40K, 41G, 42L, 44K, 46E, 161E, 185E, 195D, 327S, 345E and 360T. All of these residues have entropies higher than 2.63 when all 235 bacteria species are considered, which means each residue shows variability of at least 60% of the theoretical maximum variability (4.392). These residues represent putative binding sites that may be the key distinguishing factors of *L. fermentum* PS150 EF-Tu in terms of its brain health effects.

Binding sites of a protein are usually exposed or they will be upon conformational change. To assess whether any of the highly variable residues detected in the previous section are situated on the exposed part of the 3D protein structure of EF-Tu, a homology model for the protein was constructed. Mapping of highly variable residues onto homology modeled 3D EF-Tu protein structure revealed that residues 40K, 41G, 42L, 44K, 46E and 327S are located on the surface of the molecule. It is interesting to note that residues 40K, 41G, 42L, 44K, and 46E are continuous punctuated only at residues 43A and 45A. In fact, both residues 43A and 45A also show high variability with entropy values of 2.004 and 2.578 respectively but these values are below the cutoff threshold. Although residue 327S is also highly variable, it is situated far away from residues 40 to 46. The other residues, 161E, 185E, 195D, 345E and 360T are embedded within the EF-Tu molecule itself.

Example 6 Sleep-Promoting Effects of PS150

Figure 13:
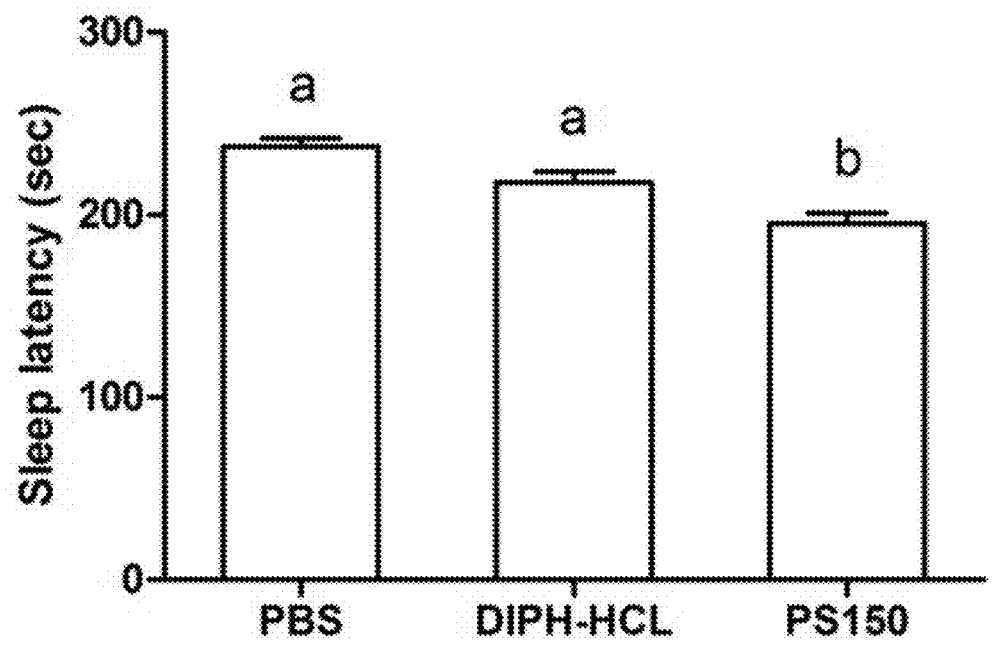
FIGS. 13 (a) and (b) show the effect of PS150 on sleep latency (a) and sleep duration (b) in pentobarbital-induced sleeping test. PBS group, where mice were fed with 200 μL phosphate buffer saline (PBS; pH 7.4); DIPH-HCL group, where mice were given 200 μL PBS containing 20 mg/kg diphenhydramine hydrochloride; PS150 group, where mice were given 200 μL PBS containing $1 \times 10^9$ cfu viable L. fermentum PS150. Error bars represent standard of means; n=10. $^{ab}$ A significant difference of the sleep latency (a) and sleep duration (b) of mice between different groups; P<0.05.
Figure 13:
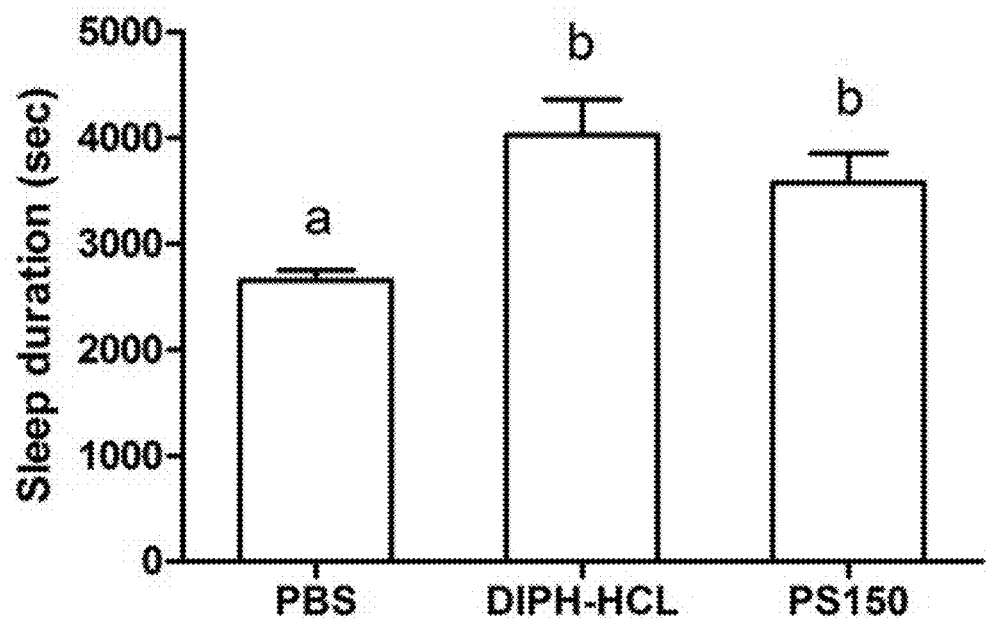

The BALB/c mice were administrated orally once daily with $10^9$ CFU/mice L. fermentum PS150 for 14 consecutive days. Control mice were tested in parallel with the animals being given PBS only. The positive control group was given DIPH-HCL (diphenhydramine hydrochloride, 20 mg/kg) as a positive control. Body weight (BW) was measured daily during the fourteen day experimental period. In the fourteenth day, sodium pentobarbital (50 mg/kg) was intraperitoneally (i.p.) injected to each mice after 30 min of intragastric (i.g.) administration of PBS, PS150 and DIPH-HCL, to test the duration of pentobarbital induced sleep. Each mouse was observed for the latency and duration of sleep. The time elapsed between pentobarbital injection and loss of righting reflex was recorded as sleep latency, and that elapsed between loss and recovery of righting reflex was recorded as sleeping duration. FIG. 13 shows the effect of PS150 on sleep latency (a) and sleep duration (b) in pentobarbital-induced sleeping test. The results show that PS150 can reduce sleep latency time and increase sleep duration.

What is claimed is:

1. A method for treating a mood disorder, a neurological condition, comprising administering to a subject lactic acid bacteria (LAB) cells thereby treating a mood disorder or a neurological condition, or inhibiting apoptosis of neurons in the subject,
wherein the LAB cells are *Lactobacillus fermentum* PS150, which has been deposited with Deutsche Sammlung von Mikroorganismen and Zellkulturen under Budapest Treaty on 6 Jun. 2016 and was given the accession number DSM 32323; wherein the LAB cells are in an amount ranging from about $10^5$ to about $10^{13}$ colony forming units (cfu); and
wherein the mood disorder or the neurological condition is selected from the group consisting of anxiety, depression, stress, sleep disturbance, memory lapses, and cognitive disorders.

2. The method of claim 1, wherein the LAB cells can lower the expression of indoleamine 2,3-dioxygenase (IDO), reduce the turnover rate of tryptophan to kynurenine, increase the serotonin level or reduce the plasma corticosterone level.

3. The method of claim 1, wherein the cognitive disorder is cognitive decline.

4. The method of claim 1, wherein the cognitive disorder is cognitive impairment.

5. The method of claim 1, wherein the cognitive disorder is mild cognitive impairment (MCI).

* * * * *

SEQUENCE LISTING

<160> NUMBER OF SEQ ID NOS: 7

<210> SEQ ID NO 1
<211> LENGTH: 486
<212> TYPE: DNA
<213> ORGANISM: Lactobacillus fermentum

<400> SEQUENCE: 1

```
atgaggaaca atcaaagtaa cacgccgcta atttcagtga ttattcctgc atataaagtc      60
gaaaaatact tagcgttttg tgttgaatca gttgttgcac aaactttaac tggttatgaa     120
gtgattattg tcgatgatgg ctcaccagat aatactggag agatcacgga tcacttagcg     180
caacaatatg aagcggttaa ggtgattcat caagaaaacg caggagttag taccgcacgg     240
aatacgggga ttgacaacgc tcaagggaaa tatattactt ttattgatgg tgatgatttt     300
atcgctccga cttttctgga gtatatggtt aatatggtag agaaaaccca ttcggatttc     360
ggactggctc tagattgttt tacgaagaat gatgagaaac ctttggatca aactgaagat     420
aaagtgtatg ctccagaaaa ggcggtaagt ttgttgctat ccccacgtgt aattgttggc     480
tgttag                                                                486
```

<210> SEQ ID NO 2
<211> LENGTH: 987
<212> TYPE: DNA
<213> ORGANISM: Lactobacillus fermentum

<400> SEQUENCE: 2

```
atgaatgatg ttccatcacc gtactatgat gaaattatag aacggggttc aaaaatattc      60
attctgccgc caataaataa cgtttaccat cattatcagg aatgcaaaaa gatattacga     120
gatggggatt acgatgttgt ttgtgataac aacttgatta aatccatccc aatgatgctt     180
gctgctaaga aatgtggagt tcctgtacgg attttgcata gtcacaacac gaaattaagc     240
acaatcatca agaaggaatg gattacgaag ctcctattgc cattattgaa aagggaaatt     300
acagattatt gtgcatgcgg ccaactagct gggaagcac tatttgggaa agctaagttt     360
acggttattc caaatgtaat ctcaccagaa acgaacacct ttgataaagt caagagagat     420
aaaatcagaa aagagcttgg cgttgacgat aaggttgttg tagggactgt tggtcggaca     480
tctatacaaa aaaacccctta tttcgcaatt gatgtaattg agaaggtaca ccaaagtaat     540
cctagtattg tttattggtg gattggtagt ggtgaactag atgatcaact gagagcgtac     600
gtagaaaaga aggggttagg taaggttgta tctttcctag gaagtaggga tgatgttcaa     660
gatctttacc aggcaatgga tgtattcttt ttaccctcgc tttttgaagg tttaccacta     720
```

```
actggagttg aagctcaagc aatggggtta ccgtcgattt tatcagctag cgttacagat    780
agattggtat ataccgatct ggtaaagtac gtatcgttgg atgaacctat cgaagaatgg    840
gaaaaagctt ttaaaaaagc gatcgaacgg attccacaaa ggagggcata tacagaagaa    900
cttaagcaga gcgtttattc agctgaagat gcgggaaaga atatgacaaa gatttacgag    960
gatcttctcg cctcaaaatt gcggtaa                                        987

<210> SEQ ID NO 3
<211> LENGTH: 1086
<212> TYPE: DNA
<213> ORGANISM: Lactobacillus fermentum

<400> SEQUENCE: 3
atgattcgga tattacaatt accaaacact atttctcgag aaaatggtcg catgtcagta     60
attatgagta tatataggca catagataga accaagattc agtttgattt tgcggtatct    120
gagtctagtg gcgatactta tcttgatgaa attaaaaagc ttggaggcaa ggtatttgtg    180
attccatctg gcgaggtttc ctacaaaagt gttgtcaaga tggttaatat gctccttaag    240
aaaagagagt attcatttat acattatcac gcaatctcaa tttggggagt tgctctaaac    300
gttgcacatc ggcatggtgt aaagataatc acacacagtc atgcaacata ttttagcgat    360
ggatttatga agtcaattcg aaatcgaatc ttttctctaa atataaagtt atattcagat    420
aagttggcag ctgtttcccc agaagcgggt agaactttat ttgaaaaaca acaatatata    480 tataaccaa atgtaattaa ttataaaaaa tatactttct cgcgtaataa tagagaaaaa    540
attcgtcggc aatataacat tgatgatggt gactttgtcg ttggtcatgt aggacgtctg    600
tcaaaacaaa aaaccatca atttctgatc agagccttta gtctattaca tgcatcggcg    660
gaaaagtaca aattaatgct cgtgggtagt ggaccactcg aaaatgatct gaggacactt    720
gtaagtcaac tgaatattga aggtcagtt attttttgttg gtgcaaagca agatgtaact    780
gcgttttatt cagcatttga cttgttctgg ttaccttcct tgtatgaggg attgcctacg    840
gttggattgg aagcgcaggc taacggtctt tcaatcattg caagtgatcg tatttcacct    900
gagctagcca ttgaaaatgt tattttttct ccaattaggc ataaaagcga tttacaaaaa    960
tggtgtcata tcactctgga gcgagattgg cctcgctcta cagatgtcat gcggacgatt   1020
gaacatagtc ggtataatta tcaacatgtc ttagatcaat ggaaaagcct atatgatatg   1080
aagtaa                                                              1086

<210> SEQ ID NO 4
<211> LENGTH: 396
<212> TYPE: PRT
<213> ORGANISM: Lactobacillus fermentum

<400> SEQUENCE: 4

Met Ala Glu Lys Glu His Tyr Glu Arg Thr Lys Pro His Val Asn Ile
1               5                   10                  15

Gly Thr Ile Gly His Val Asp His Gly Lys Thr Leu Thr Ala Ala
            20                  25                  30

Ile Thr Lys Val Leu Ala Ala Lys Gly Leu Ala Lys Ala Glu Asp Tyr
        35                  40                  45

Ser Asp Ile Asp Ala Ala Pro Glu Glu Lys Glu Arg Gly Ile Thr Ile
    50                  55                  60

Asn Thr Ala His Val Glu Tyr Glu Thr Glu Lys Arg His Tyr Ala His
65                  70                  75                  80
```

```
Ile Asp Ala Pro Gly His Ala Asp Tyr Val Lys Asn Met Ile Thr Gly
                85                  90                  95
Ala Ala Gln Met Asp Gly Ala Ile Leu Val Val Ala Ala Thr Asp Gly
            100                 105                 110
Pro Met Pro Gln Thr Arg Glu His Ile Leu Leu Ala Arg Gln Val Gly
        115                 120                 125
Val Glu Tyr Ile Val Val Phe Leu Asn Lys Thr Asp Leu Val Asp Asp
    130                 135                 140
Asp Glu Leu Val Asp Leu Val Glu Met Glu Val Arg Asp Leu Leu Ser
145                 150                 155                 160
Glu Tyr Asp Phe Pro Gly Asp Asp Val Pro Val Val Arg Gly Ser Ala
                165                 170                 175
Leu Lys Ala Leu Glu Gly Asp Pro Glu Gln Glu Gln Val Val Leu His
            180                 185                 190
Leu Leu Asp Val Val Asp Glu Tyr Ile Pro Thr Pro Lys Arg Pro Thr
        195                 200                 205
Asp Lys Pro Phe Met Met Pro Val Glu Asp Val Phe Thr Ile Thr Gly
    210                 215                 220
Arg Gly Thr Val Ala Ser Gly Arg Ile Asp Arg Gly Thr Val Lys Ile
225                 230                 235                 240
Gly Asp Glu Val Glu Ile Val Gly Leu Lys Glu Asp Val Ile Lys Ser
                245                 250                 255
Thr Val Thr Gly Val Glu Met Phe His Lys Thr Leu Asp Leu Gly Glu
            260                 265                 270
Ala Gly Asp Asn Val Gly Val Leu Leu Arg Gly Val Ser His Asp Gln
        275                 280                 285
Ile Glu Arg Gly Gln Val Leu Ala Glu Pro Gly Ser Ile Gln Thr His
    290                 295                 300
Lys Gln Phe Lys Gly Glu Val Tyr Val Met Thr Lys Glu Glu Gly Gly
305                 310                 315                 320
Arg His Thr Pro Phe Phe Ser Asn Tyr Arg Pro Gln Phe Tyr Phe His
                325                 330                 335
Thr Thr Asp Val Thr Gly Thr Ile Glu Leu Pro Asp Gly Val Glu Met
            340                 345                 350
Val Met Pro Gly Asp Asn Val Thr Phe Thr Val Glu Leu Gln Lys Pro
        355                 360                 365
Val Ala Leu Glu Lys Gly Leu Lys Phe Thr Ile Arg Glu Gly Gly His
    370                 375                 380
Thr Val Gly Ala Gly Val Val Ser Glu Val Leu Asp
385                 390                 395

<210> SEQ ID NO 5
<211> LENGTH: 1540
<212> TYPE: DNA
<213> ORGANISM: Lactobacillus fermentum

<400> SEQUENCE: 5
tcaggatgaa cgccggcggt gtgcctaata catgcaagtc gaacgcgttg gcccaattga      60
ttgatggtgc ttgcacctga ttgattttgg tcgccaacga gtggcggacg ggtgagtaac     120
acgtaggtaa cctgcccaga agcggggggac aacatttgga aacagatgct aataccgcat     180
aacaacgttg ttcgcatgaa caacgcttaa aagatggctt ctcgctatca cttctggatg     240
gacctgcggt gcattagctt gttggtgggg taacggccta ccaaggcgat gatgcatagc     300
cgagttgaga gactgatcgg ccacaatggg actgagacac ggcccatact cctacgggag     360
```

```
gcagcagtag ggaatcttcc acaatgggcg caagcctgat ggagcaacac cgcgtgagtg    420
aagaagggtt tcggctcgta aagctctgtt gttaaagaag aacacgtatg agagtaactg    480
ttcatacgtt gacggtattt aaccagaaag tcacggctaa ctacgtgcca gcagccgcgg    540
taatacgtag gtggcaagcg ttatccggat ttattgggcg taaagagagt gcaggcggtt    600
ttctaagtct gatgtgaaag ccttcggctt aaccggagaa gtgcatcgga aactggataa    660
cttgagtgca gaagagggta gtggaactcc atgtgtagcg gtggaatgcg tagatatatg    720
gaagaacacc agtggcgaag gcggctacct ggtctgcaac tgacgctgag actcgaaagc    780
atgggtagcg aacaggatta gataccctgg tagtccatgc cgtaaacgat gagtgctagg    840
tgttggaggg tttccgccct tcagtgccgg agctaacgca ttaagcactc cgcctgggga    900
gtacgaccgc aaggttgaaa ctcaaaggaa ttgacggggg cccgcacaag cggtggagca    960
tgtggtttaa ttcgaagcta cgcgaagaac cttaccaggt cttgacatct gcgccaacc    1020 ctagagatag gcgtttcct tcgggaacgc aatgacaggt ggtgcatggt cgtcgtcagc    1080
tcgtgtcgtg agatgttggg ttaagtcccg caacgagcgc aacccttgtt actagttgcc    1140
agcattaagt tgggcactct agtgagactg ccggtgacaa accggaggaa ggtggggacg    1200
acgtcagatc atcatgcccc ttatgacctg gctacacac gtgctacaat ggacggtaca    1260
acgagtcgcg aactcgcgag gcaagcaaa tctcttaaaa ccgttctcag ttcggactgc    1320
aggctgcaac tcgcctgcac gaagtcggaa tcgctagtaa tcgcggatca gcatgccgcg    1380
gtgaatacgt tcccgggcct tgtacacacc gcccgtcaca ccatgagagt ttgtaacacc    1440
caaagtcggt ggggtaacct tttaggagcc agccgcctaa ggtgggacag atgattaggg    1500
tgaagtcgta caaggtagc cgtaggagaa cctgcggttg                          1540

<210> SEQ ID NO 6
<211> LENGTH: 401
<212> TYPE: DNA
<213> ORGANISM: Lactobacillus fermentum

<400> SEQUENCE: 6
aagacacctt ctacgtgacc ccgtctgttt tgatgcggac ccaaacgtcg ccaatgcagg     60
cccggatgct ggaacaacac gacttctcca aggggccgtt gaagatgatc tcaccgggga    120
aggtttaccg ccgcgacacc gatgacgcta cccacagcca ccaattccac caggttgaag    180
gaatcgtggt cggtgaacac gtcacgatgg cagatttaaa ggggaccta gaggcagtgg    240 cccaaaacct gtttggcgac cagctcaagg tgcgtctgcg cccgagttac ttcccgttca    300
cggaaccgtc cgtcgaggcc gacatcactt gctttaattg cctgggggcc ggttgctcaa    360
tctgtaaggg gactggttgg atcgaggtgt tgggggccgg c                        401

<210> SEQ ID NO 7
<211> LENGTH: 1190
<212> TYPE: DNA
<213> ORGANISM: Lactobacillus fermentum

<400> SEQUENCE: 7
atggcagaaa aagaacatta tgaacgtact aagccccacg ttaacatcgg tactattggc     60
cacgttgacc acgggaagac tactttaacc gcagctatca ccaaggtatt ggccgctaag    120
ggccttgcca aggcagaaga ctactctgat atcgatgctg ctccagaaga aaaggaacgt    180
ggtatcacta tcaacactgc ccacgttgaa tacgaaacgg aaaagcgtca ctacgctcac    240
```

-continued

```
atcgacgctc cagggcacgc cgactacgtt aagaacatga tcactggggc cgctcaaatg    300
gacggtgcga tcttagttgt tgccgcaact gatggtccga tgccacaaac tcgtgaacac    360
atccttctgg ctcgccaggt cggtgttgaa tacatcgttg tcttccttaa caagactgac    420
cttgttgacg atgacgaact ggttgactta gttgaaatgg aagttcgtga ccttctgtcc    480
gaatacgact tccctggcga tgatgttccg gttgttcgtg ggtccgctct taaggccctc    540
gaaggtgacc cagaacaaga acaagttgtt cttcaccttc tggacgtcgt tgacgaatac    600
atcccaactc caaagcgtcc tactgacaag ccattcatga tgcctgtcga agacgtcttc    660
actatcactg gtcgtggtac tgttgcttct ggtcgtatcg accgtggtac tgttaagatc    720
ggtgacgaag ttgaaatcgt tggtttgaag gaagacgtta tcaagtccac tgttaccggt    780
gttgaaatgt tccacaagac ccttgatctt ggggaagccg gggacaacgt cggtgtcctt    840
ttacgtgggg tttctcacga ccaaatcgaa cgtggtcaag ttctggcaga accaggctcc    900
atccaaacgc acaagcaatt caagggtgaa gtctacgtta tgaccaagga agaaggggc    960 cgtcacacgc cattcttctc caactaccgc ccacaattct acttccacac tactgacgtt    1020
actggtacca ttgaactccc agatggtgtt gaaatggtta tgcctggtga caacgttacc    1080
ttcactgttg aactgcaaaa gccagttgcc cttgaaaagg gtctgaagtt caccatccgt    1140
gaaggtggtc acactgttgg tgccggtgtg gtatccgaag tgctcgacta              1190
```